United States Patent
Garcia et al.

(10) Patent No.: US 10,059,947 B2
(45) Date of Patent: Aug. 28, 2018

(54) NUCLEIC ACIDS AND METHODS FOR THE TREATMENT OF POMPE DISEASE

(71) Applicant: SYNTHENA AG, Bern (CH)

(72) Inventors: Luis Garcia, Bailly (FR); Aurelie Avril, Jouy-en-Josas (FR)

(73) Assignee: SYNTHENA AG, Bern (CH)

( * ) Notice: Subject to any disclaimer, the term of this patent is extended or adjusted under 35 U.S.C. 154(b) by 0 days.

(21) Appl. No.: 14/917,118

(22) PCT Filed: Sep. 10, 2014

(86) PCT No.: PCT/EP2014/069325
§ 371 (c)(1),
(2) Date: Mar. 7, 2016

(87) PCT Pub. No.: WO2015/036451
PCT Pub. Date: Mar. 19, 2015

(65) Prior Publication Data
US 2016/0215291 A1 Jul. 28, 2016

(30) Foreign Application Priority Data

Sep. 11, 2013 (EP) ..................................... 13184013

(51) Int. Cl.
*C12N 15/113* (2010.01)
*C12N 15/11* (2006.01)
(52) U.S. Cl.
CPC ........ *C12N 15/1137* (2013.01); *C12N 15/111* (2013.01); *C12Y 302/0102* (2013.01); *C12N 2310/11* (2013.01); *C12N 2310/315* (2013.01); *C12N 2310/321* (2013.01); *C12N 2320/33* (2013.01)
(58) Field of Classification Search
CPC .......................... C12N 15/111; C12N 2320/33
See application file for complete search history.

(56) References Cited

U.S. PATENT DOCUMENTS 5,646,265 A * 7/1997 McGee .................. C07H 19/04
536/25.34
6,582,908 B2 * 6/2003 Fodor .................. B01J 19/0046
435/288.3
2004/0214255 A1 * 10/2004 Heichman .............. C07K 14/47
435/14
2015/0197534 A1 * 7/2015 Wilton ............... C12N 15/1137
514/90

FOREIGN PATENT DOCUMENTS

| WO | WO2006/021724 A2 | 3/2006 |
| WO | WO2011/113889 A1 | 9/2011 |
| WO | WO2015/035231 A1 | 3/2015 |

OTHER PUBLICATIONS

B. J. Byrne et al: "Pompe disease gene therapy", Human Molecular Genetics 20(R1):684-696 (2011).
A. Dardis et al: "Functional characterization of the common c.-32-13T>G mutation of GAA gene: identification of potential therapeutic agents", Nucleic Acids Research 42(2):1291-1302 (2013).
F. Desmet et al: "Human Splicing Finder: an online bioinformatics tool to predict splicing signals," Nucleic Acids Research 37(9):1-14 (2009).
G. Douillard-Guilloux et al: "Restoration of muscle functionality by genetic suppression of glycogen synthesis in a murine model of Pompe disease", Human Molecular Genetics 19(4):684-696 (2009).
Giancarlo Parenti: "New strategies for the treatment of lysosomal storage diseases (Review)", International Journal of Molecular Medicine, Nov. 19, 2012, DOI: 10.3892/ijmm.2012.1187.
A. Goyenvalle et al: "Rescue of Dystrophic Muscle Through U7 snRNA-Mediated Exon Skipping," Science 306:1796-1799 (2004).
A. Goyenvalle et al: "Enhanced Exon-skipping Induced by U7 snRNA Carrying a Splicing Silencer Sequence: Promising Tool for DMD Therapy," Molecular Therapy 17(7):1234-1240 (2009).
M. Kroos et al: "The Genotype-Phenotype Correlation in Pompe Disease," American Journal of Medical Genetics Part C 160C:59-68 (2012).
S. Takikita et al: "Murine muscle cell models for Pompe disease and their use in studying therapeutic approaches", Molecular Genetics and Metabolism 96(4):208-217 (2009).
S. Zampieri et al: "Splicing mutations in glycogen-storage disease type II: evaluation of the full spectrum of mutations and their relation to patients' phenotypes", European Journal of Human Genetics 19(4):422-431 (2011).

\* cited by examiner

*Primary Examiner* — J. E. Angell
(74) *Attorney, Agent, or Firm* — Medler Ferro Woodhouse & Mills PLLC

(57) ABSTRACT

The invention relates to nucleic acids and methods for restoring acid alpha-glucosidase (GAA) activity in patients with Pompe disease using splice-switching technology.

22 Claims, 7 Drawing Sheets

Specification includes a Sequence Listing.

NUCLEIC ACIDS AND METHODS FOR THE TREATMENT OF POMPE DISEASE

FIELD OF THE INVENTION

The invention relates to nucleic acids and methods for restoring acid alpha-glucosidase (GAA) activity in patients with Pompe disease using splice-switching technology. In particular, the invention provides methods to allow normal inclusion of exon 2 into the GAA mRNA in Pompe patients with the c.-32 IVS1-13 T>G mutation causing deleterious skipping of exon 2, which encompasses the ATG start codon of the GAA transcript. More specifically, the invention relates to a method for assembly of a functional GAA mRNA by means of antisense oligonucleotides compatible with systemic delivery in order to access all affected tissues throughout the body (skeletal muscles, heart and liver). Such an approach meets the therapeutic needs of over half of all adult Caucasian patients with Pompe disease.

BACKGROUND

Pompe disease (or glycogen storage disease type II—GSD II) is caused by pathogenic mutations in the acid α-glucosidase gene (GAA) located on chromosome 17. The GAA gene spans over 20,000 base pairs. It contains 20 exons giving rise to a full length mRNA of about 3.6 kb, translated from the initiation codon located in exon 2 as an inactive precursor of about 110 kD, which is further processed in mature forms of 70-77 kD. The mode of inheritance of the disease is recessive: patients have two pathogenic mutations in the acid α-glucosidase gene, one on each allele. Basically, the very nature of the mutations affecting the GAA gene together with the combination of the mutant alleles determine the level of residual lysosomal acid α-glucosidase activity and subsequent clinical severity. In most cases, a combination of two alleles with fully deleterious mutations leads to virtual absence of acid α-glucosidase activity and to the severe classic infantile phenotype. A severe mutation in one allele and a milder mutation in the other result in a slower progressive phenotype with residual activity up to 23% of average control activity. However, for these patients, enzyme activity is not always predictive of the age of onset and progression of the disease.

Hundreds of GAA mutations have been identified, but some are more common among given ethnic groups. For example:
- c.-32 IVS1-13T>G is a splice mutation found in over half of all adult Caucasian patients.
- Asp645Glu is found in most infants with Pompe disease from Taiwan.
- Arg854X nonsense mutation is found in many affected African or African-American infants.
- del525T and del exon 18 are commonly seen in Dutch infants with the disease.

Patients with the common "c.-32 IVS1-13T>G" mutation (a splicing mutation lessening dramatically, but not completely, the inclusion of exon 2 in the final transcript—leaky mutation), combined with a fully deleterious mutation on the other allele, all show significant residual enzyme activity and a protracted course of disease, but onset of symptoms varied from the 1st year of life to late adulthood (Kroos M, et al.; Am J Med Genet Part C Semin Med Genet 2012, 160C:59-68; Kroos M, et al., Neurology 2007, 68:110-115; Raben N, et al.; Hum Mol Genet, 1996, 5(7):995-1000).

Pompe disease has long been an untreatable disorder, for which only supportive care was available. In March 2006, Myozyme (manufactured by Genzyme), the first treatment for patients with Pompe disease, received marketing authorization in the European Union, followed in April 2006 by FDA approval in the United States. Myozyme is an "enzyme replacement therapy" (ERT), which is supplied by intravenous delivery of the lacking enzyme. Another approach involves gene therapy. The rationale for gene therapy is to introduce a gene encoding the replacement enzyme into the somatic cells, thus creating a permanent enzyme source. To this end, the coding sequence for human acid α-glucosidase is inserted in a viral vector. For Pompe disease, gene therapy using adenoviral (Ad), Adeno-Associated (AAV) and hybrid Ad-AAV vectors have been investigated in rat, mouse and quail. So far, preclinical results in animal models are encouraging, but sustained expression of the therapeutic transgene, prevention of antibody formation against the viral vector and/or acid α-glucosidase, as well as safety issues are still questionable. Another approach used chaperone therapy. Some of the pathogenic mutations in the acid α-glucosidase gene lead to abnormal forms of the enzyme that are poorly transported to the lysosome or are unstable in the lysosomal environment. The rationale for chaperone therapy is that some small molecules may have the property to stabilize and thus enhance the residual acid α-glucosidase activity in the lysosomes of patients with this type of mutations. The effect of chemical chaperones has so far only been tested in cultured fibroblasts from patients with Pompe disease (Okumiya, Mol Genet Metab 2007; 90:49-57).

It is apparent that although different strategies have been proposed for treating Pompe disease, as summarized above, there is still a need for an efficient therapeutic approach for treating the most common form of the disease.

SUMMARY OF THE INVENTION

The present invention relates to a nucleic acid 10 to 50 nucleotides in length, complementary to a nucleotide sequence of the acid alpha-glucosidase (GAA) pre-mRNA, said nucleic acid being able to correct the splicing of exon 2 of the acid alpha-glucosidase pre-mRNA. As will be shown below, the nucleic acid of the invention is an antisense oligonucleotide useful for treating Pompe disease. In a particular embodiment, the nucleic acid comprises a nucleotide sequence complementary to an Exonic Silencer Sequence (ESS) present in exon 2 of the pre-mRNA encoding acid alpha-glucosidase.

In a particular embodiment, the nucleic acid molecule of the invention comprises or consists of a nucleotide sequence complementary to a sequence comprised in the region defined by positions [+3;+45] of exon 2 of the human GAA gene (SEQ ID NO:1), wherein preferably said sequence comprised in the region defined by positions [+3;+45] of exon 2 of the human GAA gene (SEQ ID NO:1) has a length from 10 to 35 nucleotides, preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+45] of exon 2 of the human GAA gene (SEQ ID NO:1).

In a further preferred embodiment, the nucleic acid molecule of the invention comprises or consists of a nucleotide sequence complementary to a sequence comprised in the region defined by positions [+3;+31] of exon 2 of the human GAA gene (SEQ ID NO:1), wherein preferably said sequence comprised in the region defined by positions [+3;+31] of exon 2 of the human GAA gene (SEQ ID NO:1) has a length from 10 to 29 nucleotides, preferably from 13 to 29 nucleotides, and has, for example, a length of 10, or 15, or 20 or 25 nucleotides, and wherein further preferably said nucleotides are contiguous nucleotides in said region defined by positions [+3;+31] of exon 2 of the human GAA gene (SEQ ID NO:1).

In further preferred embodiment, the nucleic acid molecule of the invention comprises or consists of a nucleotide sequence complementary to a sequence comprised in the region defined by positions [+3;+31] of exon 2 of the human GAA gene (SEQ ID NO:1), wherein preferably said sequence comprised in the region defined by positions [+3;+31] of exon 2 of the human GAA gene (SEQ ID NO:1) has a length from 10 to 29 nucleotides, preferably from 13 to 29 nucleotides, and has, for example, a length of 10, or 15, or 20 or 25 nucleotides, and wherein said nucleotides are contiguous nucleotides in said region defined by positions [+3;+31] of exon 2 of the human GAA gene (SEQ ID NO:1).

Thus, in a preferred embodiment, the present invention provides for a nucleic acid molecule, wherein said nucleic acid molecule is 10 to 50 nucleotides in length and is complementary to a nucleotide sequence of the acid alpha-glucosidase (GAA) pre-mRNA, and wherein said nucleic acid molecule is an antisense oligonucleotide and is able to correct the splicing of exon 2 of the acid alpha-glucosidase pre-mRNA, and wherein said nucleotide sequence of the GAA pre-mRNA is a sequence comprised in the region defined by positions [+3;+45] of exon 2 of the human GAA gene (SEQ ID NO:1), and wherein preferably said sequence comprised in the region defined by positions [+3;+45] of exon 2 of the human GAA gene (SEQ ID NO:1) has a length from 10 to 35 nucleotides, preferably from 13 to 35 nucleotides or from 10 to 30 nucleotides, and has, for example, a length of 10, or 15, or 20 or 30 nucleotides, and most preferably said sequence comprised in the region defined by positions [+3;+45] of exon 2 of the human GAA gene (SEQ ID NO:1) has a length of 15 nucleotides.

In again further preferred embodiment, the present invention provides for a nucleic acid molecule, wherein said nucleic acid molecule is 10 to 50 nucleotides in length and is complementary to a nucleotide sequence of the acid alpha-glucosidase (GAA) pre-mRNA, and wherein said nucleic acid molecule is an antisense oligonucleotide and is able to correct the splicing of exon 2 of the acid alpha-glucosidase pre-mRNA, and wherein said nucleotide sequence of the GAA pre-mRNA is a sequence comprised in the region defined by positions [+3;+45] of exon 2 of the human GAA gene (SEQ ID NO:1), wherein said antisense oligonucleotide is a tc-DNA or a 2'-O-methyl-RNA, wherein the phosphate backbone of said antisense oligonucleotide is composed of solely phosphodiester linkages, solely phosphorothioate linkages or combinations of phosphodiester and phosphorothioate linkages. Preferably said antisense oligonucleotide is a tc-DNA or a 2'-O-methyl-RNA, wherein the phosphate backbone of said antisense oligonucleotide is composed of solely phosphodiester linkages. Also preferred are embodiments, wherein said antisense oligonucleotide is a tc-DNA or a 2'-O-methyl-RNA, wherein the phosphate backbone of said antisense oligonucleotide is composed of solely phosphorothioate linkages. In another preferred embodiment, said antisense oligonucleotide is a tc-DNA or a 2'-O-methyl-RNA, wherein the phosphate backbone of said antisense oligonucleotide is composed of combinations of phosphodiester and phosphorothioate linkages. Further preferably said sequence comprised in the region defined by positions [+3;+45] of exon 2 of the human GAA gene (SEQ ID NO:1) has a length from 10 to 35 nucleotides, preferably from 13 to 35 nucleotides or from 10 to 30 nucleotides, and has, for example, a length of 10, or 15, or 20 or 30 nucleotides, and most preferably said sequence comprised in the region defined by positions [+3;+45] of exon 2 of the human GAA gene (SEQ ID NO:1) has a length of 15 nucleotides.

In again further preferred embodiment, the present invention provides for a nucleic acid molecule, wherein said nucleic acid molecule is 10 to 50 nucleotides in length and is complementary to a nucleotide sequence of the acid alpha-glucosidase (GAA) pre-mRNA, and wherein said nucleic acid molecule is an antisense oligonucleotide and is able to correct the splicing of exon 2 of the acid alpha-glucosidase pre-mRNA, and wherein said nucleotide sequence of the GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from 10 to 29 nucleotides, preferably from 13 to 29 nucleotides, and has, for example, a length of 10, or 15, or 20 or 25 nucleotides.

In again further preferred embodiment, the present invention provides for a nucleic acid molecule, wherein said nucleic acid molecule is 10 to 50 nucleotides in length and is complementary to a nucleotide sequence of the acid alpha-glucosidase (GAA) pre-mRNA, and wherein said nucleic acid molecule is an antisense oligonucleotide and is able to correct the splicing of exon 2 of the acid alpha-glucosidase pre-mRNA, and wherein said nucleotide sequence of the GAA pre-mRNA is a sequence comprised in the region defined by positions [+3;+31] of exon 2 of the human GAA gene (SEQ ID NO:1), wherein said antisense oligonucleotide is a tc-DNA or a 2'-O-methyl-RNA, wherein the phosphate backbone of said antisense oligonucleotide is composed of solely phosphodiester linkages, solely phosphorothioate linkages or combinations of phosphodiester and phosphorothioate linkages. Preferably said antisense oligonucleotide is a tc-DNA or a 2'-O-methyl-RNA, wherein the phosphate backbone of said antisense oligonucleotide is composed of solely phosphodiester linkages. Also preferred are embodiments, wherein said antisense oligonucleotide is a tc-DNA or a 2'-O-methyl-RNA, wherein the phosphate backbone of said antisense oligonucleotide is composed of solely phosphorothioate linkages. In another preferred embodiment, said antisense oligonucleotide is a tc-DNA or a 2'-O-methyl-RNA, wherein the phosphate backbone of said antisense oligonucleotide is composed of combinations of phosphodiester and phosphorothioate linkages. Further preferably said sequence comprised in the region defined by positions [+3;+31] of exon 2 of the human GAA gene (SEQ ID NO:1) has a length from 10 to 29 nucleotides, preferably from 13 to 29 nucleotides, and has, for example, a length of 10, or 15, or 20 or 25 nucleotides.

In particular, the nucleic acid of the invention may be complementary to one or more of the sequences defined by positions 3-17, 7-21 or 17-31 in SEQ ID NO: 1 (representing human GAA exon 2) or in a sequence having at least 90% homology with SEQ ID NO:1. In a particular embodiment, the nucleic acid molecule of the invention comprises or consists of a nucleotide sequence complementary to one or more of the sequences defined by positions [+3;+17], [+7;+21] or [+17;+31] in SEQ ID NO:1 or in a sequence having at least 90% homology with SEQ ID NO:1, in particular at least 95%, more particularly at least 99%. In a further preferred embodiment of the present invention, the nucleic acid molecule comprises or consists of a nucleotide sequence complementary to one or more of the sequences selected from (i) the sequence defined by position [+3;+17] of SEQ ID NO:1; (ii) the sequence defined by position [+7;+21] of SEQ ID NO:1; (iii) the sequence defined by position [+17;+31] of SEQ ID NO:1; (iv) a sequence having at least 90% homology, preferably at least 95% homology, and further preferably at least 99% homology with the sequence defined in either (i), (ii) or (iii). Further preferably said sequence has a length from 10 to 29 nucleotides, preferably from 13 to 29 nucleotides, and has, for example, a length of 10, or 15, or 20 or 25 nucleotides.

Thus, in a preferred embodiment, the present invention provides for a nucleic acid molecule, wherein said nucleic acid molecule is 10 to 50 nucleotides in length and is complementary to a nucleotide sequence of the acid alpha-glucosidase (GAA) pre-mRNA, and wherein said nucleic acid molecule is an antisense oligonucleotide and is able to correct the splicing of exon 2 of the acid alpha-glucosidase pre-mRNA, and wherein said nucleic acid molecule comprises or consists of a nucleotide sequence complementary to one or more of the sequences selected from (i) the sequence defined by position [+3;+17] of SEQ ID NO:1; (ii) the sequence defined by position [+7;+21] of SEQ ID NO:1; (iii) the sequence defined by position [+17;+31] of SEQ ID NO:1; (iv) the sequence defined by position [+3;+31] of SEQ ID NO:1; (v) the sequence defined by position [+3;+45] of SEQ ID NO:1; (vi) the sequence defined by position [+3;+46] of SEQ ID NO:1; (vii) a sequence having at least 90% homology, preferably at least 95% homology, and further preferably at least 99% homology with the sequence defined in any one of (i), (ii), (iii), (iv), (v) or (vi). In a further preferred embodiment, the present invention provides for a nucleic acid molecule, wherein said nucleic acid molecule is 10 to 50 nucleotides in length and is complementary to a nucleotide sequence of the acid alpha-glucosidase (GAA) pre-mRNA, and wherein said nucleic acid molecule is an antisense oligonucleotide and is able to correct the splicing of exon 2 of the acid alpha-glucosidase pre-mRNA, and wherein said nucleic acid molecule comprises or consists of a nucleotide sequence complementary to one or more of the sequences selected from (i) the sequence defined by position [+3;+17] of SEQ ID NO:1; (ii) the sequence defined by position [+7;+21] of SEQ ID NO:1; (iii) the sequence defined by position [+17;+31] of SEQ ID NO:1; (iv) a sequence having at least 90% homology, preferably at least 95% homology, and further preferably at least 99% homology with the sequence defined in either (i), (ii) or (iii). In again a further preferred embodiment, the present invention provides for a nucleic acid molecule, wherein said nucleic acid molecule is 10 to 50 nucleotides in length and is complementary to a nucleotide sequence of the acid alpha-glucosidase (GAA) pre-mRNA, and wherein said nucleic acid molecule is an antisense oligonucleotide and is able to correct the splicing of exon 2 of the acid alpha-glucosidase pre-mRNA, and wherein said nucleic acid molecule comprises or consists of a nucleotide sequence complementary to one or more of the sequences selected from (i) the sequence defined by position [+3;+17] of SEQ ID NO:1; (ii) the sequence defined by position [+7;+21] of SEQ ID NO:1; or (iii) the sequence defined by position [+17;+31] of SEQ ID NO:1.

In a particular embodiment, the nucleic acid of the invention comprises or consists of the nucleotide sequence shown in SEQ ID NO:2, SEQ ID NO:3, SEQ ID NO:4 or SEQ ID NO:5.

In a further preferred embodiment of the present invention, the nucleic acid molecule comprises or consists of a nucleotide sequence complementary to one or more of the sequences selected from (i) the sequence of SEQ ID NO:2; (ii) the sequence of SEQ ID NO:3; (iii) the sequence of SEQ ID NO:4; (iv) the sequence of SEQ ID NO:5; (v) the sequence of SEQ ID NO:12; or (vi) the sequence of SEQ ID NO:13.

In another aspect, the present invention provides for a nucleic acid molecule being able to restore the normal splicing of exon 2 of the human acid alpha-glucosidase (GAA) pre-mRNA displaying the c.-32-13T>G mutation, wherein said nucleic acid molecule comprises or consists of an antisense oligonucleotide, wherein said antisense oligonucleotide is complementary to a nucleotide sequence of said human acid alpha-glucosidase (GAA) pre-mRNA, wherein said nucleotide sequence of said GAA pre-mRNA is a sequence comprised in the region defined by positions [+3;+45] of exon 2 of the human GAA gene (SEQ ID NO:1), and wherein preferably said sequence comprised in the region defined by positions [+3;+45] of exon 2 of the human GAA gene (SEQ ID NO:1) has a length from 10 to 100 nucleotides, preferably from 10 to 50 nucleotides, further preferably a length from 10 to 35 nucleotides, again further preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+45] of exon 2 of the human GAA gene (SEQ ID NO:1).

The present invention also relates to the nucleic acid as defined above, for use in a method for the treatment of Pompe disease. The patients treated are those whose genome comprises a mutation preventing the inclusion of exon 2 of the GAA pre-mRNA within the mature GAA mRNA. In particular, the patient carries the c.-32 IVS1-13 T>G mutation or a IVS1.-3 C>N (wherein N may be A, T or G, in particular A or G) mutation in intron 1 of the gene coding GAA. Very preferably, the patient carries the c.-32-13 T>G mutation in intron 1 of the gene coding GAA. Typically and very preferred, the patient is a human patient and said human patient harbours at least one copy of the c.-32-13 T>G mutation in the GAA gene. Thus, in a further aspect, the present invention provides for the inventive nucleic acid molecule, as defined herein, for use in a method for the treatment of Pompe disease in a patient, wherein said patient is a human patient and said human patient harbours at least one copy of the c.-32-13 T>G mutation in the GAA gene. Further preferably, said nucleic acid molecule comprises, or preferably consists of, a nucleotide sequence complementary to a sequence comprised in the region defined by positions [+3;+45] of exon 2 of the GAA gene. In a very preferred embodiment, the present invention provides for the inventive nucleic acid molecule, as defined herein, for use in a method for the treatment of Pompe disease in a patient, wherein said patient is a human patient and said human patient harbours at least one copy of the c.-32-13 T>G mutation in the GAA gene, wherein preferably said nucleic acid molecule comprises, or preferably consists of, a nucleotide sequence complementary to a sequence comprised in the region defined by positions [+3;+31] of exon 2 of the GAA gene, and wherein said nucleic acid molecule is an antisense oligonucleotide.

In a very preferred embodiment, the nucleic acid of the invention comprises or consists of the nucleotide sequence shown in SEQ ID NO:14, SEQ ID NO:15, SEQ ID NO:16 or SEQ ID NO:17.

The invention further relates to a method for treating Pompe disease caused by non inclusion of exon 2, in particular Pompe disease caused by the c.-32 IVS1-13 T>G mutation in the GAA gene, in a patient in need thereof, comprising the step of administering to said patient a nucleic acid as defined above. The nucleic acid improves inclusion of said exon 2 during splicing.

This invention also relates to a method for correcting Pompe disease caused by a mutation preventing the inclusion of exon 2 of the GAA pre-mRNA within the mature GAA mRNA, in particular the c.-32 IVS1-13 T>G mutation, by using in vivo delivery of either gene vectors encoding engineered snRNAs such as U1 or U7 snRNAs harbouring the antisense sequences provided herein, or engineered autologous myogenic cells, with said optimized snRNAs, such as mesangioblasts, AC 133+ cells or any mesenchymal stem cells for correction of the glycogen storage dysfunction.

The invention further relates to a pharmaceutical composition comprising the nucleic acid of the invention.

DETAILED DESCRIPTION OF THE INVENTION

Throughout the specification, several terms are employed and are defined in the following paragraphs as well as throughout the specification.

The terms "splicing" and "exon inclusion" are known to the skilled person in the art, and used herein accordingly. The term "splicing", as used herein, refer to the modification of a pre-mRNA following transcription, in which introns are removed and exons are joined. The term "exon inclusion", as used herein, refers to the process leading to the inclusion into the fully-processed mRNA of an exon which would have been otherwise left out of the mature mRNA due to a splicing defect.

The term "antisense oligonucleotide" refers to a single strand of DNA or RNA that is complementary to a chosen sequence. An antisense oligonucleotide is capable of hybridizing to a pre-mRNA or an mRNA having a complementary coding or non coding nucleotide sequence.

The term "complementary", as used herein, refers to a nucleic acid sequence that can form hydrogen bond(s) with another nucleic acid sequence by either traditional Watson-Crick base pairing or other non-traditional types of pairing (e.g., Hoogsteen or reversed Hoogsteen hydrogen bonding) between complementary nucleosides or nucleotides.

In reference to the nucleic acid molecules of the present invention, and in particular in reference to the nucleic acid molecules of the present invention being antisense oligonucleotides, the binding free energy for an inventive nucleic acid molecule with its complementary sequence is sufficient to allow the relevant function of the inventive nucleic acid molecule to proceed and there is a sufficient degree of complementarity to avoid non-specific binding of the inventive nucleic acid molecule to non-target sequences under conditions in which specific binding is desired, i.e., under physiological conditions in the case of ex vivo or in vivo therapeutic treatment. Determination of binding free energies for nucleic acid molecules is well known in the art (see e.g., Turner et al., CSH Symp Quant Biol, 1987, LI/:123-133; Freier et al., Proc Nat Acad Sci USA 1986, 83:9373-9377; and Turner et al., J Am Chem Soc, 1987, 109:3783-3785). Thus, "complementary", as used herein, indicate a sufficient degree of complementarity or precise pairing such that stable and specific binding occurs between the inventive nucleic acid molecule and the target nucleotide sequence of the pre-mRNA.

It is understood in the art that a nucleic acid molecule need not be 100% complementary to a target nucleic acid sequence to be complementary. That is, two or more nucleic acid molecules may be less than fully complementary. Complementarity is indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths. One of ordinary skill in the art would recognize that the inventive nucleic acid molecule provided herein is at least 80%, preferably at least 85%, further preferably at least 90%, again further preferably at least 93%, again further preferably at least 96%, again further preferably at least 98%, and most preferably 100% complementary to the target nucleotide sequence of the pre-mRNA.

Thus, the inventive nucleic acid molecule and the target nucleotide sequence of the pre-mRNA are complementary to each other when a sufficient number of corresponding positions in each molecule are occupied by nucleobases that can bond with each other to allow stable association between the inventive nucleic acid molecule and the target nucleotide sequence of the pre-mRNA as indicated above. One skilled in the art recognizes that the inclusion of mismatches is possible without eliminating the ability of the oligomeric compounds to remain in association. Therefore, described herein are inventive nucleic acid molecules, preferably being antisense oligonucleotides, that may comprise up to about 20% nucleotides that are mismatched (i.e., are not nucleobase complementary to the corresponding nucleotides of the target). Preferably the inventive nucleic acid molecules, preferably being antisense oligonucleotides, contain no more than about 15%, more preferably not more than about 10%, most preferably not more than 5% or no mismatches.

The term "acid alpha-glucosidase" (also called: lysosomal alpha-glucosidase or α-1,4-glucosidase) has its general meaning in the art and refers to a protein (e.g. enzyme) that in humans is encoded by the GAA gene. Errors in this gene cause glycogen storage disease type II (Pompe disease). The GAA enzyme is essential for the degradation of glycogen to glucose in lysosomes.

The terms "c.-32 IVS1-13 T>G" and "c.-32-13 T>G" are interchangeably used herein, and refer to the same mutation in the GAA gene (den Dunnen J T, et al.; Hum Genet. 2001; 109:121-124).

In the context of the invention, the term "patient" refers to any subject, afflicted with Pompe disease and harbouring at least one copy of the GAA gene comprising a mutation preventing inclusion of exon 2 in the mRNA. In particular, the patient harbours at least one copy of the c.-32 IVS1-13 T>G mutation or of a IVS1.-3 C>N (wherein N may be A, T or G, in particular A or G) mutation in the GAA gene. Further preferred, the patient harbours at least one copy of the c.-32-13 T>G mutation in the GAA gene. Typically and very preferred, the patient is a human patient and said human patient harbours at least one copy of the c.-32-13 T>G mutation in the GAA gene.

In its broadest meaning, the term "treating" or "treatment" refers to reversing, alleviating, inhibiting the progress of, or preventing the disorder or condition to which such term applies, or one or more symptoms of such disorder or condition.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The inventors herein show that splice-switching strategies can be used for the treatment of patients with Pompe disease. In particular, a significant subset of patients with Pompe disease, particularly those harbouring at least one copy of the c.-32 IVS1-13 T>G mutation, may be treated thanks to the present invention. The inventors demonstrate unprecedented efficient GAA restoration in cells from patients treated ex vivo with antisense oligomers targeting key domains of the GAA pre-mRNA for rescuing inclusion of exon 2 in the mature mRNA.

Those of skill in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack is involved in a disease process, disease symptoms may be monitored and/or measured in order to indirectly detect the presence or absence of a correctly functioning protein, or to gauge the success of a treatment protocol intended to remedy the lack of the protein. Particularly, the rescue of GAA in cells from patients with Pompe disease (e.g. c.-32 IVS1-13 T>G mutation or an IVS1.-3 C>N mutation) can be measured by several methods recognized. For example, by using RT-PCR for assessing the presence of the full length GAA mRNA (i.e. including exon 2), or testing GAA activity by measuring levels of glycogen deposits in cells.

As will be understood by those of skill in the art, in the cell nucleus, eukaryotic genes are transcribed into pre-messenger RNAs (pre-mRNA), which contain both exons and introns. To form mature mRNA, splicing occurs at specific sequences at the borders of exons and introns (splice sites) thereby removing introns and connecting exons to one another to form mRNA, which is translated into protein. During the two last decades, splice-switching approaches have been developed to interfere with such mechanisms. In particular, successful inclusion of exon 7 of the SMN2 gene has been reported by using antisense oligonucleotides masking an intronic splice silencer (ISS) spanning from nucleotide 10 to 25 in intron 7. However, no information in the prior art is available indicating that inclusion of exon 2 in the GAA RNA could be obtained by targeting ESS sequences in said exon 2.

In the present invention, the protein that is stabilized or restored to function is the acid alpha-glucosidase (GAA). More specifically, exon-encoded sequences are force-included using an antisense oligonucleotide (AON). In this case, an AON is designed to complement suitable sequences, in particular RNA sequences within the pre-mRNA molecule, which lower correct splicing of the targeted exon(s), thereby blocking sequences that may harbour negative CIS-elements, such as intronic splice silencers (ISS) or exonic splice silencers (ESS), which would exclude the targeted exon(s) into mature mRNA.

In the present invention, AON sequences are selected so as to be specific, i.e. the AON's are complementary only to the sequences of the targeted pre-mRNA and not to other nucleic acid sequences. The AON's used in the practice of the invention may be of any suitable type, e.g. oligodeoxyribonucleotides, oligoribonucleotides, morpholinos, tricyclo-DNA-antisense oligonucleotides, tricyclo-phosphorothioate DNA, LNA, U7- or U1-modified AONs or conjugate products thereof such as peptide-conjugated or nanoparticle-complexed AONs, which are known to the skilled person in the art (Bell, N M, et al., ChemBioChem, 2009, 10:2691-2703 and references cited therein). AONs employed in the practice of the invention are generally from about 10 to about 35 nucleotides in length, in particular from about 13 to about 35 nucleotides or from about 10 to about 30 nucleotides, and may be for example, about 10, or about 15, or about 20 or about 30 nucleotides or more in length. Typically, morpholino-AONs are about 25-30 nucleotides long, 2'PMO-AONs are about 20-25 nucleotides long, and tricyclo-AONs are about 13-20 nucleotides long, U7 and U1-modified AONs may possibly carry longer antisense sequences of about 50 nucleotides.

In particular object of this invention relates to a nucleic acid molecule as described herein, linked to a modified U7 or U1 small nuclear RNA (snRNA). Information on U7 modification can in particular be found in Goyenvalle A, et al., Science 2004, 306:1796-1799; Goyenvalle A, et al., Mol Ther, 2009 7:1234-1240; Denti M A, et al., Hum Gene Ther, 2006 17(5):565-574; Gedicke-Hornung C, et. al., EMBO Mol Med, 2013 5(7):1060-1077; Hoogaars W M, et al., Hum Gene Ther, 2012 23(12):1269-1279, Vulin A, et al., Mol Ther, 2012 20(11):2120-2133; Goyenvalle A, et al., Hum Mol Genet, 2012 21(11):2559-2571; Goyenvalle A, et al., Mol Ther, 2012 20(6):1212-1221, François V, et al., Nat Struct Mol Biol, 2011 18(1):85-87; Quenneville S P, et al., Mol Ther, 2007 15(2):431-438; WO11113889; WO06021724; and references cited therein. The various modifications of snRNA of U1 or U7, preferably of U7, useful for the present invention are known for the skilled person in the art and, by way of example, some of them are exemplified in the given literature.

U7 snRNA is normally involved in histone pre-mRNA 3'-end processing, but can be converted into a versatile tool for splicing modulation by a small change in the binding site for Sm/Lsm proteins. The antisense sequence embedded into a snRNP particle is therefore protected from degradation and accumulates in the nucleus where splicing occurs.

The terms "engineered Ux snRNA" or "modified Ux snRNA", as interchangeably used herein, refer to (i) the optimizing of the promoter driving the transcription of the engineered Ux snRNA, wherein optimizing can be enhancing or reducing the activity of the promoter, typically and preferably enhancing the activity of the promoter; (ii) optimizing the "sm" domain of the natural snRNA, wherein optimizing encompasses, as indicated herein and in the cited references, the proper subcellular localization where splicing occurs; (iii) the natural antisense domain of the Ux snRNA is replaced by the "on purpose" antisense sequence, thus capable to anneal the targeted pre-mRNA, and thus by the preferred nucleic acid molecules of the present invention.

Thus, in a preferred embodiment of the present invention, said nucleic acid molecule is linked to a modified Ux snRNA, preferably to a modified U7 or U1 snRNA, and further preferably said nucleic acid molecule is linked to a modified U7 snRNA, and again further preferably said nucleic acid molecule is linked to a modified U7SmOPT snRNA, wherein the SmOPT sequence is provided in FIG. 7 and refers to position 30 to 40 of SEQ ID NO: 18.

Thus, in a further preferred embodiment of the present invention, said nucleic acid molecule useful for treating Pompe disease, wherein said nucleic acid molecule comprises or consists of an antisense oligonucleotide, wherein said antisense oligonucleotide is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein said sequence comprised in the region defined by positions [+3;+31] of exon 2 of the human GAA gene (SEQ ID NO:1) has a length from 10 to 29 nucleotides, and wherein said nucleic acid molecule is linked to a modified U7 or U1 snRNA, and wherein preferably said nucleic acid molecule is linked to a modified U7 snRNA.

In an again further preferred embodiment of the present invention, said nucleic acid molecule useful for treating Pompe disease, wherein said nucleic acid molecule comprises or consists of an antisense oligonucleotide, wherein said antisense oligonucleotide is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein said sequence comprised in the region defined by positions [+3;+31] of exon 2 of the human GAA gene (SEQ ID NO:1) has a length from 10 to 29 nucleotides, and wherein said nucleic acid molecule is linked to a modified U7 snRNA, wherein preferably said modified modified U7 snRNA is a modified U7SmOPT snRNA, wherein the SmOPT sequence refers to position 30 to 40 of SEQ ID NO: 18.

In another preferred embodiment of the present invention, said nucleic acid molecule is able to restore the normal splicing of exon 2 of the human acid alpha-glucosidase (GAA) pre-mRNA, wherein said nucleic acid molecule comprises or consists of an antisense oligonucleotide, wherein said antisense oligonucleotide is complementary to a nucleotide sequence of said human acid alpha-glucosidase (GAA) pre-mRNA, wherein said nucleotide sequence of said GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from about 10 to about 29 nucleotides, preferably from about 13 to about 29 nucleotides, and has, for example, a length of about 10, or about 15, or about 20 or about 25 nucleotides. The term "able to restore the normal splicing of exon 2 of the human acid alpha-glucosidase (GAA) pre-mRNA", as used and described in detail herein, refers to the correct splicing of intron 1 allowing the formation of a complete GAA mRNA, which can be translated into a fully functional protein (ATG starting codon is in exon 2: missing exon 2 makes that the delta2-mRNA cannot be translated into human acid alpha-glucosidase).

In another preferred embodiment of the present invention, said nucleic acid molecule is able to restore the normal splicing of exon 2 of the human acid alpha-glucosidase (GAA) pre-mRNA displaying the c.-32-13T>G mutation, wherein said nucleic acid molecule comprises or consists of an antisense oligonucleotide, wherein said antisense oligonucleotide is complementary to a nucleotide sequence of said human acid alpha-glucosidase (GAA) pre-mRNA, wherein said nucleotide sequence of said GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from about 10 to about 29 nucleotides, preferably from about 13 to about 29 nucleotides, and has, for example, a length of about 10, or about 15, or about 20 or about 25 nucleotides.

In again another aspect, the present invention provides for a nucleic acid molecule is able to restore the normal splicing of exon 2 of the human acid alpha-glucosidase pre-mRNA displaying the c.-32-13T>G mutation, wherein said nucleic acid molecule comprises or consists of an antisense oligonucleotide, wherein said antisense oligonucleotide is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein said sequence comprised in the region defined by positions [+3;+31] of exon 2 of the human GAA gene (SEQ ID NO:1) has a length from 10 to 29 nucleotides, and wherein said nucleic acid molecule is linked to a modified U7 or U1 snRNA, and wherein preferably said nucleic acid molecule is linked to a modified U7 snRNA.

In again another aspect, the present invention provides for a nucleic acid molecule is able to restore the normal splicing of exon 2 of the human acid alpha-glucosidase pre-mRNA displaying the c.-32-13T>G mutation, wherein said nucleic acid molecule comprises or consists of an antisense oligonucleotide, wherein said antisense oligonucleotide is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein said sequence comprised in the region defined by positions [+3;+31] of exon 2 of the human GAA gene (SEQ ID NO:1) has a length from 10 to 29 nucleotides, and wherein said nucleic acid molecule is linked to a modified U7 snRNA, wherein preferably said modified U7 snRNA is a modified U7SmOPT snRNA, wherein the SmOPT sequence refers to position 30 to 40 of SEQ ID NO: 18.

In a further aspect, the present invention provides for a vector comprising the nucleic acid molecule of the invention. Preferably, said vector comprises a nucleic acid molecule able to restore the normal splicing of exon 2 of the human acid alpha-glucosidase pre-mRNA displaying the c.-32-13T>G mutation, wherein said nucleic acid molecule comprises or consists of an antisense oligonucleotide, wherein said antisense oligonucleotide is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein said sequence comprised in the region defined by positions [+3;+31] of exon 2 of the human GAA gene (SEQ ID NO:1) has a length from 10 to 29 nucleotides, and wherein said nucleic acid molecule is linked to a modified U7 snRNA, wherein preferably said modified U7 snRNA is a modified U7SmOPT snRNA, wherein the SmOPT sequence refers to position 30 to 40 of SEQ ID NO: 18. Further preferably, said vector is selected from plasmids, adenoviral vectors, associated-adenoviral vectors and lentiviral vectors, preferably from adenoviral vectors, associated-adenoviral vectors. Thus, in a very preferred embodiment, said vector is an adenoviral vector or an associated-adenoviral vector and comprises a nucleic acid molecule able to restore the normal splicing of exon 2 of the human acid alpha-glucosidase pre-mRNA displaying the c.-32-13T>G mutation, wherein said nucleic acid molecule comprises or consists of an antisense oligonucleotide, wherein said antisense oligonucleotide is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein said sequence comprised in the region defined by positions [+3;+31] of exon 2 of the human GAA gene (SEQ ID NO:1) has a length from 10 to 29 nucleotides, and wherein said nucleic acid molecule is linked to a modified U7 snRNA, wherein said modified U7 snRNA is a modified U7SmOPT snRNA, wherein the SmOPT sequence refers to position 30 to 40 of SEQ ID NO: 18.

In another aspect, the present invention provides for an isolated eukaryotic cell transfected by the inventive vector, and wherein said cell is preferably a skeletal muscle cell, a myoblast or a cell capable of muscle differentiation.

In another aspect, the present invention provides for a pharmaceutical composition comprising the inventive vector or the inventive cell. In a further aspect, the present invention provides for the inventive vector or the inventive cell as a medicament. In again another aspect, the present invention provides for the inventive vector for treating Pompe disease. In another aspect, the present invention provides for the inventive cell for treating Pompe disease. In again another aspect, the present invention provides for a method of restoring the function of human acid alpha-glucosidase by inclusion of exon 2 comprising the step of contacting a cell with the inventive vector.

An object of the invention relates to a nucleic acid molecule complementary to a nucleic acid sequence 5' in exon 2 of a GAA gene, the nucleic acid molecule being able to set free the acceptor splice site of exon 2 from a strong hairpin formed when the GAA gene comprises a point mutation resulting in exon 2 exclusion from the mRNA such as the c.-32 IVS1-13 T>G or an IVS1.-3 C>N mutation.

Another object of the invention relates to a nucleic acid molecule complementary to a nucleic acid sequence of a GAA gene, this nucleic acid molecule being able to correct splicing of exon 2 of the GAA pre-mRNA. The present invention relates in particular to a nucleic acid molecule (or otherwise referred to as an antisense oligonucleotide in the present application) complementary to exon 2 of a GAA gene, in particular to a 5' region of exon 2, said nucleic acid molecule comprising a nucleotide sequence complementary to one or more Exonic Silencer Sequence(s) (ESS) in exon 2 of the gene coding for acid alpha-glucosidase. Said nucleic acid molecule is thus capable of masking the ESSs in exon 2 and therefore promotes inclusion of said exon in the mRNA coding acid alpha-glucosidase. ESS sequences recruit splicing inhibitors on the pre-mRNA. Masking of these sequences may therefore decrease this recruitment and promote inclusion of exon 2 in the mRNA. ESS may be found in a given sequence searching for consensus sequences. In particular, one may use the Human Splicing Finder bioinformatics tool in identifying such ESS (Desmet et al., 2009, Human Splicing Finder: an online bioinformatics tool to predict splicing signals, Nucleic Acids Research, 2009, 1-14; www.umd.be/HSF/).

The present inventors show that a nucleic acid molecule of the invention, which is a molecule targeting one or several ESS in exon 2, is able to restore inclusion of said exon 2 in the mRNA of patients carrying a mutation of the GAA that would result in the exclusion of said exon 2 in the absence of the nucleic acid molecule of the invention.

Therefore, in an embodiment of the present invention, the nucleic acid molecule is 10 to 50 nucleotides in length, and complementary to a nucleotide sequence of the acid alpha-glucosidase pre-mRNA, wherein said nucleic acid is able to correct the splicing of exon 2 of the acid alpha-glucosidase pre-mRNA, and wherein said nucleic acid molecule comprises a nucleotide sequence complementary to the Exonic Silencer Sequence (ESS) in exon 2 of the gene coding for acid alpha-glucosidase.

In a particular embodiment, the nucleic acid molecule of the invention comprises a nucleotide sequence complementary to a sequence comprised in the region defined by positions +3 +45 of exon 2 of the GAA gene. In a further particular embodiment, the nucleic acid molecule of the invention comprises a nucleotide sequence complementary to a sequence comprised in the region defined by positions [+3;+31] of exon 2 of the human GAA gene. In a particular embodiment, the nucleic acid molecule of the invention comprises or consists of a nucleotide sequence complementary to one or more of the sequences defined by positions 3-17, 7-21 or 17-31 in SEQ ID NO:1 or in a sequence having at least 90% homology with SEQ ID NO:1, in particular at least 95%, more particularly at least 99%. In a further preferred embodiment of the present invention, the nucleic acid molecule comprises or consists of a nucleotide sequence complementary to one or more of the sequences selected from (i) the sequence defined by position [+3;+17] of SEQ ID NO:1; (ii) the sequence defined by position [+7;+21] of SEQ ID NO:1; (iii) the sequence defined by position [+17;+31] of SEQ ID NO:1; (iv) a sequence having at least 90% homology, preferably at least 99% homology with the sequence defined in either (i), (ii) or (iii).

In a more particular embodiment, said nucleic acid molecule is complementary to the nucleotide sequence shown in SEQ ID NO:2, SEQ ID NO:3, SEQ ID NO:4, SEQ ID NO:5, SEQ ID NO:12 or SEQ ID NO:13.

```
                                                SEQ ID NO: 2
5'-CUGUAGGAGCUGUCC-3'

SEQ ID NO: 3
5'-AGGAGCUGUCCAGGC-3'

SEQ ID NO: 4
5'-CAGGCCAUCUCCAAC-3'

SEQ ID NO: 5
5'-CUGUAGGAGCUGUCCAGGCCAUCUCCAACCAUGGGAGUGAGGCA-3'

SEQ ID NO: 12
5'-CUGUAGGAGCUGUCCAGGCCAUCUCCAAC-3'

SEQ ID NO: 13
5'-CUGUAGGAGCUGUCCAGGCCAUCUCCAACCAUGGGAGUGAGGC-3'
```

The antisense oligonucleotides (AONs) of the invention can be synthesized de novo using any of a number of procedures well known in the art. For example, the b-cyanoethyl phosphoramidite method (Beaucage, S. L., and Caruthers, M. H., Tet. Let. 22:1859, 1981); nucleoside H-phosphonate method (Garegg et al., Tet. Let. 27:4051-

4054, 1986; Froehler et al., Nucl. Acid. Res. 14:5399-5407, 1986; Garegg et al., Tet. Let. 27:4055-4058, 1986, Gaffney et al., Tet. Let. 29:2619-2622, 1988). These chemistries can be performed by a variety of automated nucleic acid synthesizers available in the market. These nucleic acids may be referred to as synthetic nucleic acids. Alternatively, AON's can be produced on a large scale in plasmids, (see Sambrook, T., et al., "Molecular Cloning: A Laboratory Manual", Cold Spring Harbor laboratory Press, New York, 1989). AON's can be prepared from existing nucleic acid sequences using known techniques, such as those employing restriction enzymes, exonucleases or endonucleases. AON's prepared in this manner may be referred to as isolated nucleic acids.

For use in vivo, the AONs may be stabilized. A "stabilized" AON refers to an AON that is relatively resistant to in vivo degradation (e.g. via an exo- or endo-nuclease). Stabilization can be a function of length or secondary structure. Alternatively, AON stabilization can be accomplished via phosphate backbone modifications. Preferred stabilized AON's of the instant invention have a modified backbone, e.g. have phosphorothioate linkages to provide maximal activity and protect the AON from degradation by intracellular exo- and endo-nucleases. Other possible stabilizing modifications include phosphodiester modifications, combinations of phosphodiester and phosphorothioate modifications, methylphosphonate, methyl-phosphorothioate, phosphorodithioate, p-ethoxy, and combinations thereof. Chemically stabilized, modified versions of the AON's also include "Morpholinos" (phosphorodiamidate morpholino oligomers, PMOs), 2'-O-Met oligomers, tricyclo (tc)-DNA oligomers (WO2010/115993), tricyclo(tc)-phosphorothioate DNA oligomers (WO2013/053928), LNAs etc, which are all known to the skilled person in the art (Bell, N M, et al., ChemBioChem, 2009, 10:2691-2703 and references cited therein).

The term "tricyclo-DNA (tc-DNA)" refers to a class of constrained oligodeoxyribonucleotide analogs in which each nucleotide is modified by the introduction of a cyclopropane ring to restrict conformational flexibility of the backbone and to optimize the backbone geometry of the torsion angle γ as (Ittig D, et al., Nucleic Acids Res, 2004, 32:346-353; Ittig D, et al., Prague, Academy of Sciences of the Czech Republic. 1:21-26 (Coll. Symp. Series, Hocec, M., 2005); Ivanova et al., Oligonucleotides 2007, 17:54-65; Renneberg D, et al., Nucleic Acids Res, 2002, 15 30:2751-2757; Renneberg D, et al., Chembiochem, 2004, 5:1114-1118; and Renneberg D, et al., JACS, 2002, 124:5993-6002). In detail, the tc-DNA differs structurally from DNA by an additional ethylene bridge between the centers C(3') and C(5') of the nucleosides, to which a cyclopropane unit is fused for further enhancement of structural rigidity as shown in the following formula ("tc-nucleoside"):

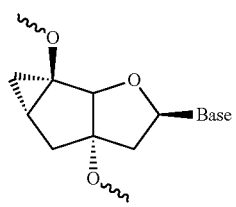

The terms "phosphorothioate linkage" or "phosphorothioate modification", as interchangeably used herein, refers to a 5' . . . -O-P(S)-O- . . . 3' moiety between two adjacent nucleosides in a nucleic acid molecule.

Thus, the term "tricyclo-phosphorothioate DNA (tc-PS-DNA)" refers to tc-DNA, wherein at least two adjacent tc-nucleosides, preferably more than two adjacent tc-nucleosides, and most preferably all tc-nucleosides, are joined by inter nucleoside phosphorothioate linkages. If other modifications are present they include phosphodiester, methylphosphonate, methyl-phosphorothioate, phosphorodithioate, and p-ethoxy modifications, and combinations thereof.

In a further preferred embodiment, said nucleic acid molecule comprises or consists of tricyclo-DNA-antisense oligonucleotides, and wherein preferably said nucleic acid molecule comprises or consists of a sequence selected from SEQ ID NO: 14, SEQ ID NO: 15, SEQ ID NO: 16, and SEQ ID NO: 17.

In a further aspect, the present invention provides for a nucleic acid molecule useful for treating Pompe disease comprising or consisting of an antisense oligonucleotide, wherein said antisense oligonucleotide is a tc-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+45] of exon 2 of the human GAA gene (SEQ ID NO:1), and wherein preferably said sequence comprised in the region defined by positions [+3;+45] of exon 2 of the human GAA gene (SEQ ID NO:1) has a length from 10 to 35 nucleotides, preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+45] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17.

In a further aspect, the present invention provides for a nucleic acid molecule useful for treating Pompe disease comprising or consisting of an antisense oligonucleotide, wherein said antisense oligonucleotide is a tc-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from about 10 to about 29 nucleotides, preferably from about 13 to about 29 nucleotides, and has, for example, a length of about 10, or about 15, or about 20 or about 25 nucleotides, and wherein further preferably said nucleotides are contiguous nucleotides in said region defined by positions [+3;+31] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17.

In a further aspect, the present invention provides for a nucleic acid molecule able to correct the splicing of exon 2 of the human acid alpha-glucosidase pre-mRNA, wherein said nucleic acid molecule comprises or consists of an antisense oligonucleotide, wherein said antisense oligonucleotide is a tc-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+45] of exon 2 of the human GAA gene (SEQ ID NO:1), and wherein preferably said sequence comprised in the region defined by positions [+3;+45] of exon 2 of the human GAA gene (SEQ ID NO:1) has a length from 10 to 50 nucleotides, preferably from 10 to 35 nucleotides, preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+45] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17.

In a further aspect, the present invention provides for a nucleic acid molecule able to correct the splicing of exon 2 of the human acid alpha-glucosidase pre-mRNA, wherein said nucleic acid molecule comprises or consists of an antisense oligonucleotide, wherein said antisense oligonucleotide is a tc-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from 10 to 35 nucleotides, further preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+31] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17.

In an another aspect, the present invention provides for a nucleic acid molecule able to restore the normal splicing of exon 2 of the human acid alpha-glucosidase pre-mRNA displaying the c.-32-13T>G mutation, wherein said nucleic acid molecule comprises or consists of an antisense oligonucleotide, wherein said antisense oligonucleotide is a tc-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+45] of exon 2 of the human GAA gene (SEQ ID NO:1), and wherein preferably said sequence comprised in the region defined by positions [+3;+45] of exon 2 of the human GAA gene (SEQ ID NO:1) has a length from 10 to 35 nucleotides, preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+45] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17.

In an another aspect, the present invention provides for a nucleic acid molecule able to restore the normal splicing of exon 2 of the human acid alpha-glucosidase pre-mRNA displaying the c.-32-13T>G mutation, wherein said nucleic acid molecule comprises or consists of an antisense oligonucleotide, wherein said antisense oligonucleotide is a tc-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from about 10 to about 29 nucleotides, preferably from about 13 to about 29 nucleotides, and has, for example, a length of about 10, or about 15, or about 20 or about 25 nucleotides, and wherein further preferably said nucleotides are contiguous nucleotides in said region defined by positions [+3;+31] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17.

In a further preferred embodiment, said nucleic acid molecule comprises or consists of tricyclo-phosphorothioate DNA-antisense oligonucleotides, and wherein preferably said nucleic acid molecule comprises or consists of a sequence selected from SEQ ID NO: 14, SEQ ID NO: 15, SEQ ID NO: 16, and SEQ ID NO: 17.

In a further aspect, the present invention provides for a nucleic acid molecule useful for treating Pompe disease comprising or consisting of an antisense oligonucleotide, wherein said antisense oligonucleotide is a tc-PS-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+45] of exon 2 of the human GAA gene (SEQ ID NO:1), and wherein preferably said sequence comprised in the region defined by positions [+3;+45] of exon 2 of the human GAA gene (SEQ ID NO:1) has a length from 10 to 35 nucleotides, preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+45] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17. In further preferred embodiments, all tc-nucleosides of said tc-PS-DNA are joined by inter nucleoside phosphorothioate linkages.

In a further aspect, the present invention provides for a nucleic acid molecule useful for treating Pompe disease comprising or consisting of an antisense oligonucleotide, wherein said antisense oligonucleotide is a tc-PS-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from about 10 to about 29 nucleotides, preferably from about 13 to about 29 nucleotides, and has, for example, a length of about 10, or about 15, or about 20 or about 25 nucleotides, and wherein further preferably said nucleotides are contiguous nucleotides in said region defined by positions [+3;+31] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17. In further preferred embodiments, all tc-nucleosides of said tc-PS-DNA are joined by inter nucleoside phosphorothioate linkages.

In a further aspect, the present invention provides for a nucleic acid molecule able to correct the splicing of exon 2 of the human acid alpha-glucosidase pre-mRNA, wherein said nucleic acid molecule comprises or consists of an antisense oligonucleotide, wherein said antisense oligonucleotide is a tc-PS-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+45] of exon 2 of the human GAA gene (SEQ ID NO:1), and wherein preferably said sequence comprised in the region defined by positions [+3;+45] of exon 2 of the human GAA gene (SEQ ID NO:1) has a length from 10 to 50 nucleotides, preferably from 10 to 35 nucleotides, preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+45] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17. In further preferred embodiments, all tc-nucleosides of said tc-PS-DNA are joined by inter nucleoside phosphorothioate linkages.

In a further aspect, the present invention provides for a nucleic acid molecule able to correct the splicing of exon 2 of the human acid alpha-glucosidase pre-mRNA, wherein said nucleic acid molecule comprises or consists of an antisense oligonucleotide, wherein said antisense oligonucleotide is a tc-PS-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from 10 to 35 nucleotides, further preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+31] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17. In further preferred embodiments, all tc-nucleosides of said tc-PS-DNA are joined by inter nucleoside phosphorothioate linkages.

In an another aspect, the present invention provides for a nucleic acid molecule able to restore the normal splicing of exon 2 of the human acid alpha-glucosidase pre-mRNA displaying the c.-32-13T>G mutation, wherein said nucleic acid molecule comprises or consists of an antisense oligonucleotide, wherein said antisense oligonucleotide is a tc-PS-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+45] of exon 2 of the human GAA gene (SEQ ID NO:1), and wherein preferably said sequence comprised in the region defined by positions [+3;+45] of exon 2 of the human GAA gene (SEQ ID NO:1) has a length from 10 to 35 nucleotides, preferably from 13 to 35 nucleotides or from 10 to 30 nucleotides, and has, for example, a length of 10, or 15, or 20 or 30 nucleotides, and wherein further preferably said nucleotides are contiguous nucleotides in said region defined by positions [+3;+45] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17. In further preferred embodiments, all tc-nucleosides of said tc-PS-DNA are joined by inter nucleoside phosphorothioate linkages.

In an another aspect, the present invention provides for a nucleic acid molecule able to restore the normal splicing of exon 2 of the human acid alpha-glucosidase pre-mRNA displaying the c.-32-13T>G mutation, wherein said nucleic acid molecule comprises or consists of an antisense oligonucleotide, wherein said antisense oligonucleotide is a tc-PS-DNA and is complementary to a nucleotide sequence of the human acid alpha-glucosidase (GAA) pre-mRNA, wherein said nucleotide sequence of the GAA pre-mRNA is a sequence comprised in the region defined by positions [+3;+31] of exon 2 of the human GAA gene (SEQ ID NO:1), and wherein preferably said sequence comprised in the region defined by positions [+3;+31] of exon 2 of the human GAA gene (SEQ ID NO:1) has a length from about 10 to about 29 nucleotides, preferably from about 13 to about 29 nucleotides, and has, for example, a length of about 10, or about 15, or about 20 or about 25 nucleotides, and wherein further preferably said nucleotides are contiguous nucleotides in said region defined by positions [+3;+31] of exon 2 of the human GAA gene (SEQ ID NO:1). Preferably said nucleic acid molecule comprises or consists of a sequence selected from SEQ ID NO: 14, SEQ ID NO: 15, SEQ ID NO: 16, and SEQ ID NO: 17. In further preferred embodiments, all tc-nucleosides of said tc-PS-DNA are joined by inter nucleoside phosphorothioate linkages.

In a very preferred embodiment of the present invention, said nucleic acid molecule comprises or consists of a sequence as set forth in SEQ ID NO: 14.

In a further very preferred embodiment of the present invention, said nucleic acid molecule comprises or consists of a sequence as set forth in SEQ ID NO: 15.

In an again a further very preferred embodiment of the present invention, said nucleic acid molecule comprises or consists of a sequence as set forth in SEQ ID NO: 16.

In a further very preferred embodiment of the present invention, said nucleic acid molecule comprises or consists of a sequence as set forth in SEQ ID NO: 17.

In a very preferred embodiment of the present invention, said nucleic acid molecule comprises or consists of a sequence as set forth in SEQ ID NO: 14, wherein said nucleic acid molecule is an antisense oligonucleotide, and wherein said antisense oligonucleotide is a tc-DNA.

In a further very preferred embodiment of the present invention, said nucleic acid molecule comprises or consists of a sequence as set forth in SEQ ID NO: 15, wherein said nucleic acid molecule is an antisense oligonucleotide, and wherein said antisense oligonucleotide is a tc-DNA.

In an again a further very preferred embodiment of the present invention, said nucleic acid molecule comprises or consists of a sequence as set forth in SEQ ID NO: 16, wherein said nucleic acid molecule is an antisense oligonucleotide, and wherein said antisense oligonucleotide is a tc-DNA.

In a further very preferred embodiment of the present invention, said nucleic acid molecule comprises or consists of a sequence as set forth in SEQ ID NO: 17, wherein said nucleic acid molecule is an antisense oligonucleotide, and wherein said antisense oligonucleotide is a tc-DNA.

In a very preferred embodiment of the present invention, said nucleic acid molecule comprises or consists of a sequence as set forth in SEQ ID NO: 14, wherein said nucleic acid molecule is an antisense oligonucleotide, and wherein said antisense oligonucleotide is a tc-PS-DNA, wherein all tc-nucleosides of said tc-PS-DNA are joined by inter nucleoside phosphorothioate linkages.

In a further very preferred embodiment of the present invention, said nucleic acid molecule comprises or consists of a sequence as set forth in SEQ ID NO: 15, wherein said nucleic acid molecule is an antisense oligonucleotide, and wherein said antisense oligonucleotide is a tc-PS-DNA, wherein all tc-nucleosides of said tc-PS-DNA are joined by inter nucleoside phosphorothioate linkages.

In an again a further very preferred embodiment of the present invention, said nucleic acid molecule comprises or consists of a sequence as set forth in SEQ ID NO: 16, wherein said nucleic acid molecule is an antisense oligonucleotide, and wherein said antisense oligonucleotide is a tc-PS-DNA, wherein all tc-nucleosides of said tc-PS-DNA are joined by inter nucleoside phosphorothioate linkages.

In a further very preferred embodiment of the present invention, said nucleic acid molecule comprises or consists of a sequence as set forth in SEQ ID NO: 17, wherein said nucleic acid molecule is an antisense oligonucleotide, and wherein said antisense oligonucleotide is a tc-PS-DNA, wherein all tc-nucleosides of said tc-PS-DNA are joined by inter nucleoside phosphorothioate linkages.

In a very preferred embodiment of the present invention, said nucleic acid molecule comprises or consists of a sequence as set forth in SEQ ID NO: 14, wherein all thymines (t) of said SEQ ID NO: 14 are substituted by uracils (u), wherein said nucleic acid molecule is an antisense oligonucleotide, and wherein said antisense oligonucleotide is a 2'-O-methyl-oligoribonucleotide. Thus, preferably, said nucleic acid molecule comprises or consists of a sequence as set forth in SEQ ID NO: 14, wherein all thymines (t) of said SEQ ID NO: 14 are substituted by uracils (u), wherein said nucleic acid molecule is a 2'-O-methyl-RNA with full phosphorothioate backbone antisense oligonucleotides (2'-O-Met). Thus, in a very preferred embodiment of the present invention, said nucleic acid molecule comprises or consists of a sequence as set forth in SEQ ID NO: 14, wherein all thymines (t) of said SEQ ID NO: 14 are substituted by uracils (u), wherein said nucleic acid molecule is an antisense oligonucleotide, and wherein said antisense oligonucleotide is a 2'-O-methyl-phosphorothioate oligoribonucleotide.

In a further very preferred embodiment of the present invention, said nucleic acid molecule comprises or consists of a sequence as set forth in SEQ ID NO: 15, wherein all thymines (t) of said SEQ ID NO: 15 are substituted by uracils (u), wherein said nucleic acid molecule is an antisense oligonucleotide, and wherein said antisense oligonucleotide is a 2'4)-methyl-oligoribonucleotide. Thus, preferably, said nucleic acid molecule comprises or consists of a sequence as set forth in SEQ ID NO: 15, wherein all thymines (t) of said SEQ ID NO: 15 are substituted by uracils (u), wherein said nucleic acid molecule is a 2'-O-methyl-RNA with full phosphorothioate backbone antisense oligonucleotides (2'-O-Met). Thus, in a further very preferred embodiment of the present invention, said nucleic acid molecule comprises or consists of a sequence as set forth in SEQ ID NO: 15, wherein all thymines (t) of said SEQ ID NO: 15 are substituted by uracils (u), wherein said nucleic acid molecule is an antisense oligonucleotide, and wherein said antisense oligonucleotide is a 2'-O-methyl-phosphorothioate oligoribonucleotide.

In an again a further very preferred embodiment of the present invention, said nucleic acid molecule comprises or consists of a sequence as set forth in SEQ ID NO: 16, wherein all thymines (t) of said SEQ ID NO: 16 are substituted by uracils (u), wherein said nucleic acid molecule is an antisense oligonucleotide, and wherein said antisense oligonucleotide is a 2'-O-methyl-oligoribonucleotide. Thus, preferably, said nucleic acid molecule comprises or consists of a sequence as set forth in SEQ ID NO: 16, wherein all thymines (t) of said SEQ ID NO: 16 are substituted by uracils (u), wherein said nucleic acid molecule is a 2'-O-methyl-RNA with full phosphorothioate backbone antisense oligonucleotides (2'-O-Met). Thus, in an again a further very preferred embodiment of the present invention, said nucleic acid molecule comprises or consists of a sequence as set forth in SEQ ID NO: 16, wherein all thymines (t) of said SEQ ID NO: 16 are substituted by uracils (u), wherein said nucleic acid molecule is an antisense oligonucleotide, and wherein said antisense oligonucleotide is a 2'-O-methyl-phosphorothioate oligoribonucleotide.

In a further very preferred embodiment of the present invention, said nucleic acid molecule comprises or consists of a sequence as set forth in SEQ ID NO: 17, wherein all thymines (t) of said SEQ ID NO: 17 are substituted by uracils (u), wherein said nucleic acid molecule is an antisense oligonucleotide, and wherein said antisense oligonucleotide is a 2'-O-methyl-oligoribonucleotide. Thus, preferably, said nucleic acid molecule comprises or consists of a sequence as set forth in SEQ ID NO: 17, wherein all thymines (t) of said SEQ ID NO: 17 are substituted by uracils (u), wherein said nucleic acid molecule is a 2'-O-methyl-RNA with full phosphorothioate backbone antisense oligonucleotides (2'-O-Met). Thus, in a further very preferred embodiment of the present invention, said nucleic acid molecule comprises or consists of a sequence as set forth in SEQ ID NO: 17, wherein all thymines (t) of said SEQ ID NO: 17 are substituted by uracils (u), wherein said nucleic acid molecule is an antisense oligonucleotide, and wherein said antisense oligonucleotide is a 2'-O-methyl-phosphorothioate oligoribonucleotide.

The terms "morpholino oligomer" or "PMO" (phosphoramidate- or phosphorodiamidate morpholino oligomer) are known to the skilled person in the art and have been described in detail (Singh Y, et al. 2010, Chem Soc Rev 39:2054-2070, as well in U.S. Pat. Nos. 5,698,685, 5,217,866, 5,142,047, 5,034,506, 5,166,315, 5,521,063, 5,506,337, 8,076,476, 8,299,206 and 7,943,762, all of which are incorporated herein by reference).

Other forms of AONs that may be used to this effect are AON sequences coupled to small nuclear RNA molecules such as U1 or U7 in combination with a viral transfer method based on, but not limited to, lentivirus or adeno-associated virus (Denti, M A, et al., Hum Gene Ther, 2008 19(6):601-608; Goyenvalle, A, et al., Science 2004 306: 1796-1799; WO11113889; WO06021724).

The invention also relates to a composition comprising a nucleic acid molecule (or AON) of the invention in a pharmaceutically acceptable carrier. In addition to AONs, pharmaceutical compositions of the present invention may also include a pharmaceutically or physiologically acceptable carrier such as saline, sodium phosphate, etc. The compositions will generally be in the form of a liquid, although this need not always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, mineral oil, etc. The formulations can also include lubricating agents, wetting agents, emulsifying agents, preservatives, buffering agents, etc. In particular, the present invention involves the administration of AONs and is thus somewhat akin to gene therapy. Those of skill in the art will recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, etc.).

The compositions of the invention are generally administered by injection, e.g. intravenously, subcutaneously or intramuscularly, although other types of administration are not precluded, e.g. inhalation, topical, per os, etc. Injectable preparations, for example, sterile injectable aqueous or oleaginous suspensions may be formulated according to the known art using suitable dispensing or wetting agents and suspending agents. The sterile injectable preparation can also be a sterile injectable solution or suspension in a nontoxic parenterally acceptable diluent or solvent, for example, as a solution in 1,3-butanediol. While delivery may be either local (i.e. in situ, directly into tissue such as muscle tissue) or systemic, usually delivery will be local to affected muscle tissue, e.g. to skeletal muscle, smooth muscle, heart muscle, etc. Depending on the form of the AONs that are administered and the tissue or cell type that is targeted, techniques such as electroporation, sonoporation, a "gene gun" (delivering nucleic acid-coated gold particles), etc. may be employed.

One skilled in the art will recognize that the amount of an AON to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the other components of a treatment protocol (e.g. administration of other medicaments such as steroids, etc.). Generally, a suitable dose is in the range of from about 1 mg/kg to about 100 mg/kg, and more usually from about 2 mg/kg to about 10 mg/kg. If a viral-based delivery of AONs is chosen, suitable doses will depend on different factors such as the viral strain that is employed, the route of delivery (intramuscular, intravenous, intra-arterial or other), but may typically range from 10e10 to 10e12 viral particles/kg. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient is usually not a single event. Rather, the AONs of the invention will likely be administered on multiple occasions, that may be, depending on the results obtained, several days apart, several weeks apart, or several months apart, or even several years apart.

With reference to the treatment of Pompe patients with the c.-32 IVS1-13 T>G mutation, the methods of the present invention can be implemented in any of several different ways. For example, the AONs of the present invention may be administered together with AONs designed to remove/include other exons from other genes (e.g. in a single mixture, or in separate mixtures but administered in close temporal proximity, such as one directly after the other—in any order—with only a few minutes or hours between administrations). Alternatively, a patient who is already under treatment using e.g. gene therapy or enzyme replacement therapy or chaperone therapy may be treated by the methods of the invention. In other words, the AONs of the invention may be administered to a patient who is already or has been receiving another treatment, but is still in need of further amelioration of the functional capabilities of the GAA molecules produced as a result of the other treatment.

If the AONs of the present invention are to be administered with AONs designed for purposes other than to improve inclusion of exon 2 of the GAA mRNA, one possible route of administration is to include sequences encoding from both types of AONs (those designed to incorporate exon 2 of the GAA pre-mRNA and those designed for another reason) in a single vector that is administered to a patient. Those of skill in the art will recognize that several vectors are available for use in delivering nucleic acid sequences so that the nucleic acid sequences may be transcribed in vivo within the recipient. Examples of such vectors include but are not limited to various vectors derived from attenuated viruses such as retroviral vectors, adenoviral vectors, adeno-associated viral vectors, HIV and influenza virus vectors, etc. Vectors based on attenuated bacteria might also be employed, e.g. mycobacterial based vectors. Those of skill in the art will recognize that if these types of methods are used, it may be preferable to avoid multiple administrations which could result in an adverse immune response to the vector.

The individuals or patients treated by the methods described herein are typically mammals, usually humans. However, this need not always be the case. Veterinary applications of this technology are also contemplated.

The following examples serve to further illustrate the invention but should not be interpreted so as to limit the invention in any way.

15 (and annealing to SEQ ID NO: 3) and AON3(tc-PS-DNA) having SEQ ID NO: 16 (and annealing to SEQ ID NO: 4), respectively.

FIG. 5B is a Western blot analysis of GAA protein expression after transfection with tricyclo-DNA antisense oligonucleotides in accordance with the present invention. Lane 1 is healthy cells. Lane 2 is untreated c.-32-13T>G cells. Lanes 3, 4 and 5 are c.-32-13T>G cells transfected with AON1(tc-PS-DNA) having SEQ ID NO: 14 (and annealing to SEQ ID NO: 2), AON2(tc-PS-DNA) having SEQ ID NO: 15 (and annealing to SEQ ID NO: 3) and AON3(tc-PS-DNA) having SEQ ID NO: 16 (and annealing to SEQ ID NO: 4), respectively. The acid alpha-glucosidase is revealed as a protein of about 70 kDa in lanes 1, 3, 4 and 5.

Figure 6:
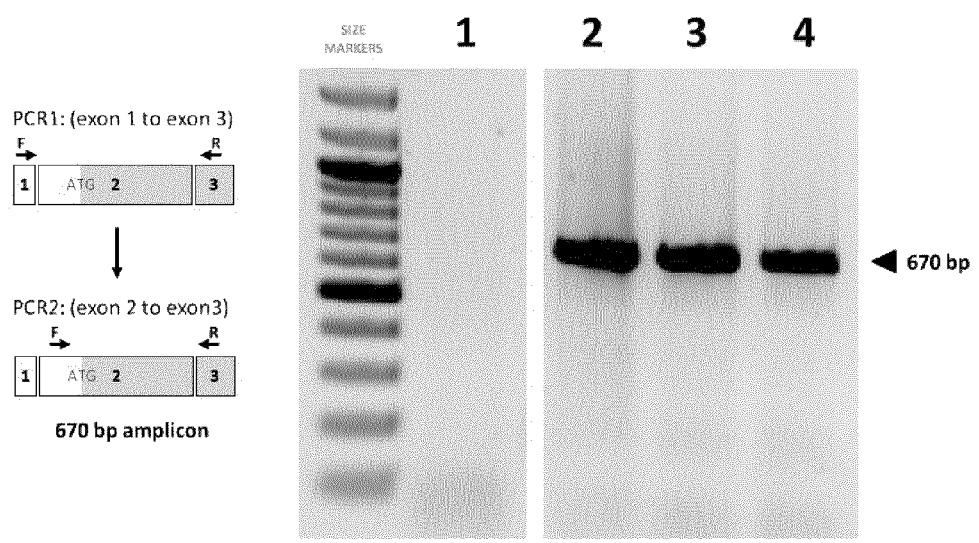

FIG. 6 is an agarose gel showing inclusion of exon 2 in GAA mRNAs in cells with the c.-32-13T>G mutation, after transfection with 2'-O-methyl-RNA with full phosphorothioate backbone antisense oligonucleotides (2'-O-Met) in accordance with the present invention. The presence of exon 2 was assessed by nested RT-PCR (PCR1 from exon 1 to exon 3, followed by PCR2 from exon 2 to exon 3 giving rise to an amplicon of 670 base pairs testifying inclusion of exon 2 in the GAA mRNA). Lane 1 is untreated c.-32-13T>G cells. Lanes 2, 3 and 4 are c.32-13T>G cells transfected with AON1(2'-O-Met) having SEQ ID NO: 14 (and annealing to SEQ ID NO: 2), AON2(2'-O-Met) having SEQ ID NO: 15 (and annealing to SEQ ID NO: 3) and AON3(2'-O-Met) having SEQ ID NO: 16 (and annealing to SEQ ID NO: 4), respectively.

Figure 7:

FIG. 7 is a schematic representation of the U7opt snRNA harbouring an antisense sequence targeting the exon 2 sequence spanning from nucleotide 3 to nucleotide 31 (U7opt-AS[+3;+31]). This U7opt snRNA with the antisense oligonucleotide is also shown in SEQ ID NO:6 (excluding the SmOPT) and SEQ ID NO: 18 (including the SmOPT as depicted in FIG. 7 and named U7opt-AS[+3;+31]).

FIG. 8A is an agarose gel showing inclusion of exon 2 in GAA mRNAs in cells with the c.-32-13T>G mutation, after transduction with a lentivector (LV) encoding U7opt-AS[+3;+31] of SEQ ID NO: 18). The presence of exon 2 was assessed by RT-PCR (from exon 1 to exon 3) giving rise to an amplicon of 635 base pairs testifying inclusion of exon 2 in the GAA mRNA. Lane 1 is healthy cells. Lane 2 is untreated c.-32-13T>G cells. Lanes 3, 4 and 5 are c.-32-13T>G cells ($25 \times 10^3$ cells) supplied with either 10 µl, 5 µl or 1 µl of LV(U7opt-AS [+3;+31]), respectively.

FIG. 8B is a Western blot analysis of GAA protein expression after transduction with LV(U7opt-AS[+3;+31]) in accordance with the present invention. Lane 1 is healthy cells. Lane 2 is untreated c.-32-13T>G cells. Lane 3 is c.-32-13T>G cells ($25 \times 10^3$ cells) supplied with 1 µl of LV(U7opt-AS[+3;+31]). The acid alpha-glucosidase is revealed as a protein of about 70 kDa in lanes 1 and 3.

EXAMPLES

Example 1

Pompe disease (also called GSD II—Glycogen Storage Disease II) is an inherited recessive disorder caused by mutations in the GAA gene encoding the acid alpha-glucosidase enzyme (also called lysosomal alpha-glucosidase or α-1,4-glucosidase), leading to engorged lysosomal glycogen accumulation and progressive muscular weakness affecting proximal limb and respiratory muscles. The disease encompasses a broad spectrum of clinical phenotypes, which differ in terms of age of onset, extent of organ involvement, and rate of progression: Infantile forms (incidence: 1/140,000) usually correlate with a more aggressive disease course and most patients die by age one; Children and adult forms (incidence: 1/60,000) are more variable across patients; always resulting in loss of ambulation, ventilation support and premature mortality.

Figure 1:
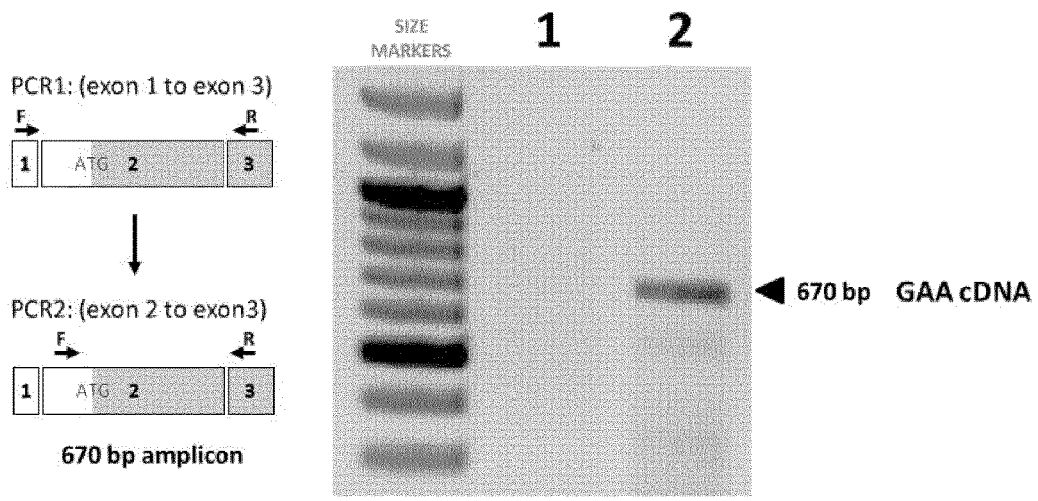
FIG. 1 is an agarose gel showing the lack of exon 2 in GAA mRNAs from c.-32 IVS1-13 T>G cells. The presence of exon 2 was assessed by nested RT-PCR (PCR1 from exon 1 to exon 3, followed by PCR2 from exon 2 to exon 3) using RNA samples extracted from either primary fibroblasts of a patient with the c.-32 IVS1-13 T>G, (Lane 1) or fibroblasts from a healthy individual (Lane 2). The amplicon of 670 base pairs testifying inclusion of exon 2 in the final GAA mRNA was not detected in the RNA extract from c.-32-13T>G cells.

Hundreds of GAA mutations have been identified, but some are more common among given ethnic groups. Among them, the c.-32 IVS1-13 T>G mutation is found in over half of all adult Caucasian patients. It is a splice mutation lessening dramatically the normal inclusion of the second exon of the GAA gene. The foremost outcome of such mis-splicing is that ensuing Δ2-GAA mRNAs (more than 90% of the GAA transcripts resulting from the mutated gene) lack their starting codon and thus cannot be translated into even semi-functional proteins (FIG. 1).

Figure 2:
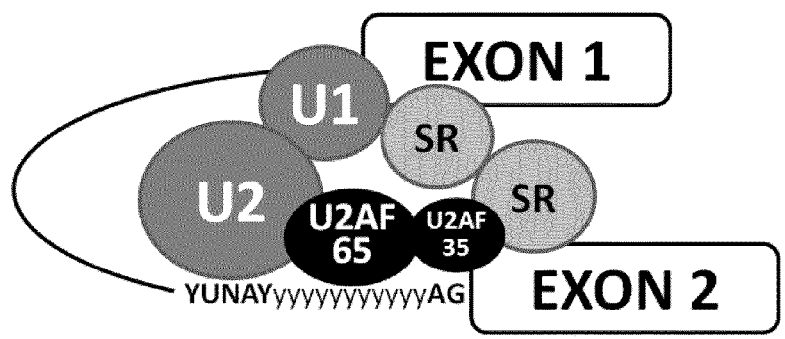
FIG. 2 is a schematic representation of the spliceosome complex.
Figure 3:
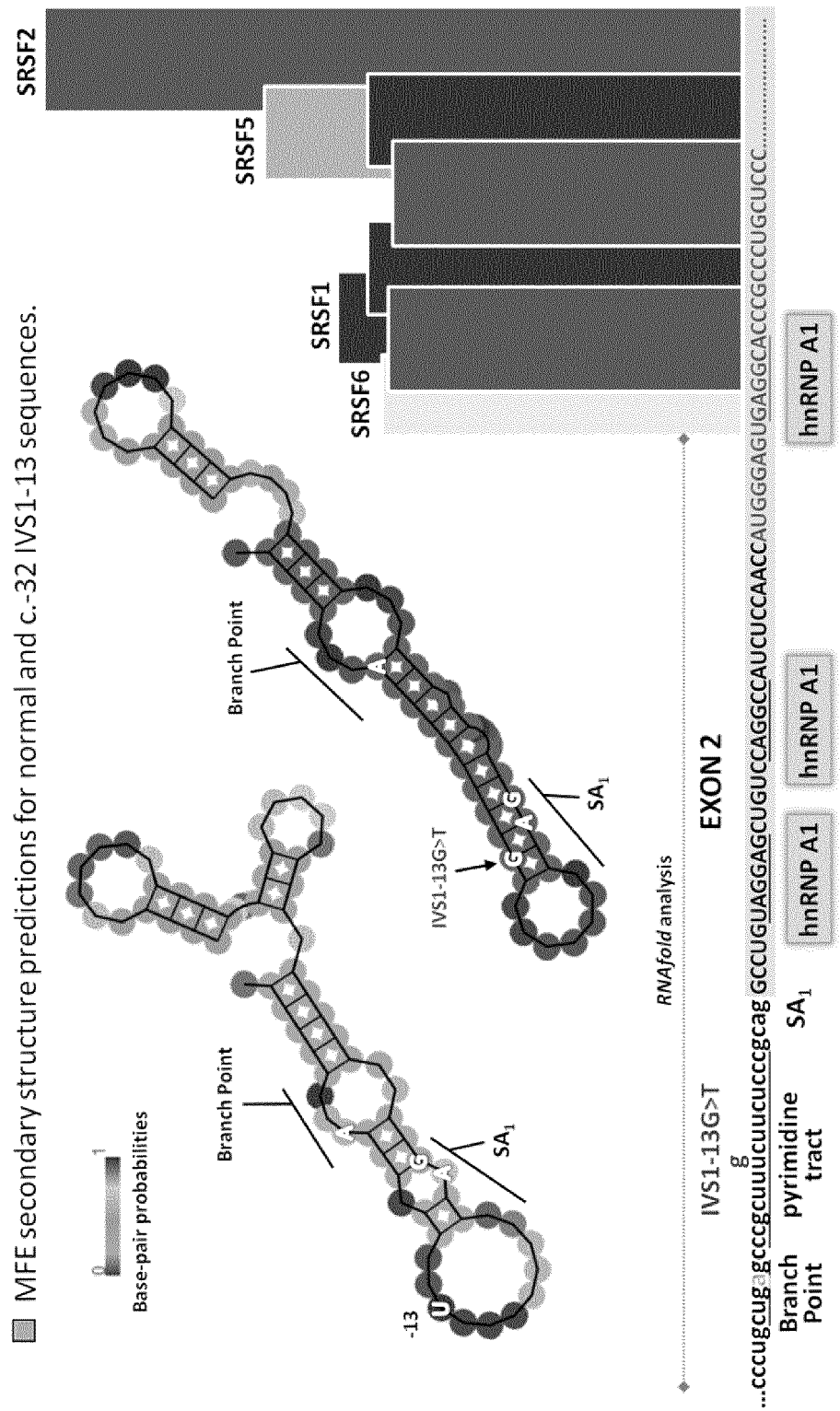
FIG. 3 is a schematic representation of splicing motives involved in the definition of exon 2 of the GAA pre-mRNA and consequences in the presence of the c.-32 IVS1-13 T>G mutation.

Splice mutations are many and varied. Most severe (e.g. totally disabling the splicing reactions) are those that typically affect the consensus donor (GU) or acceptor (AG) splicing sites at the 5' and 3' ends of introns, thus impairing transesterification reactions. Mutations which affect cis-acting regulatory elements (silencers or enhancers) and other RNA features influencing splicing are usually less severe given that resulting inhibition is often incomplete and some normal transcripts can still be synthesised. The T to G transition provoked by the c.-32 IVS1-13 mutation is one of those. It is located within the pyrimidine tract (also called polypyrimidine-Py), a series of pyrimidines (y) among the branch site (in humans the branch consensus is yUnAy) and the AG at the 3' end of the intron, which allows the recruitment of the dimeric U2 auxiliary factor protein or U2AF, identified as a major site of splicing regulation: the U2AF 65-kDa subunit interacts with the pyrimidine tract, while the smaller 35-kDa subunit directly contacts the 3' splice site sequence (FIG. 2). Therefore, a common explanation for the effect of the c.-32 IVS1-13 mutation might be that the T to G transition weakens the strength of the polypyrimidine tract, which could not any more efficiently recruit U2AF. Nonetheless, the fact that the Py consensus varies somewhat in length and sequence for every intron does not support such an assumption. Instead we hypothesised that the T to G transition might have altered the correct removal of intron 1 by modifying the secondary structure of the pre-mRNA at the level of its 3' acceptor splice site, thus making it ineffective. In order to investigate this hypothesis and develop an interventional splice correction therapy for these patients (e.g. having the c.-32 IVS1-13 mutation), we analysed the definition of the intron1/exon 2 boundary of the GAA gene and its predicted secondary structures by using the Human-Splicing-Finder (HSF) (www.umd.be/HSF/) and the RNAfold software of the ViennaRNA Web Services. FIG. 3 shows the location of the key determinants of splicing at the intron 1/exon 2 boundary, such as the branch point (cugAg), the pyrimidine tract (ccgcuuucuucuccc), the 3' splice site (SA1). It also shows the putative exonic splicing enhancer sites (ESE) to which splicing activator proteins bind, increasing the probability that a nearby site will be used as a splice junction. The HSF analysis revealed an unexpected feature of the exon 2: its 5' region (to be precise the first 40 nucleotides) was devoid of ESE sites, but displayed at least three ESSs (exonic splice silencer), which might bind splicing repressors such as the heterogeneous nuclear ribonucleoprotein A1 (hnRNP A1). The hnRNP A1 proteins are able to bind single stranded RNAs in a cooperative way, which can unwind RNA secondary structures and preferentially spreads in a 3' to 5' direction to eventually displace SR proteins bound at ESE sites. Interestingly, the RNAfold analysis showed major differences for the predicted secondary structures of the region spanning from nucleotide −30 to +39 in either normal sequence or mutated sequence (T>G in −13). In both cases, MFE (minimum free energy) predicted structures showed that this particular region of the pre-mRNA [−30;+39] could likely form a hairpin, although such a structure was reinforced in the mutant: for the normal sequence, the free energy of the thermodynamic ensemble was about −18.38 kcal/mol, the frequency of the MFE structure in the ensemble was 20.46%, and the ensemble diversity was 22.37; for the mutant sequence, the free energy of the thermodynamic ensemble was −22.02 kcal/mol, the frequency of the MFE structure in the ensemble was 36.35%, and the ensemble diversity was 9.68. These predictive structures allowed us to propose an explanation for the mechanism by which the T>G mutation takes action on the correct splicing of exon 2. First, in normal, the pre-mRNA around the acceptor splice site tends to form a hairpin potentially hindering the splice reaction. Fortunately, the strength of this hairpin would be reasonably weak and could be easily unwound by hnRNP A1 not competing with SR proteins bound a little further at 3'. Second, in mutant, the same region forms a strong hairpin that cannot be overcome by hnRNP A1. As a result, the high base-pairing probability of the nucleotides involved in this secondary structure makes almost inaccessible some crucial consensus sequences at the 3' end of intron 1, such as the acceptor splice site, the pyrimidine tract for U2AF recruitment and the branch site.

Figure 4:
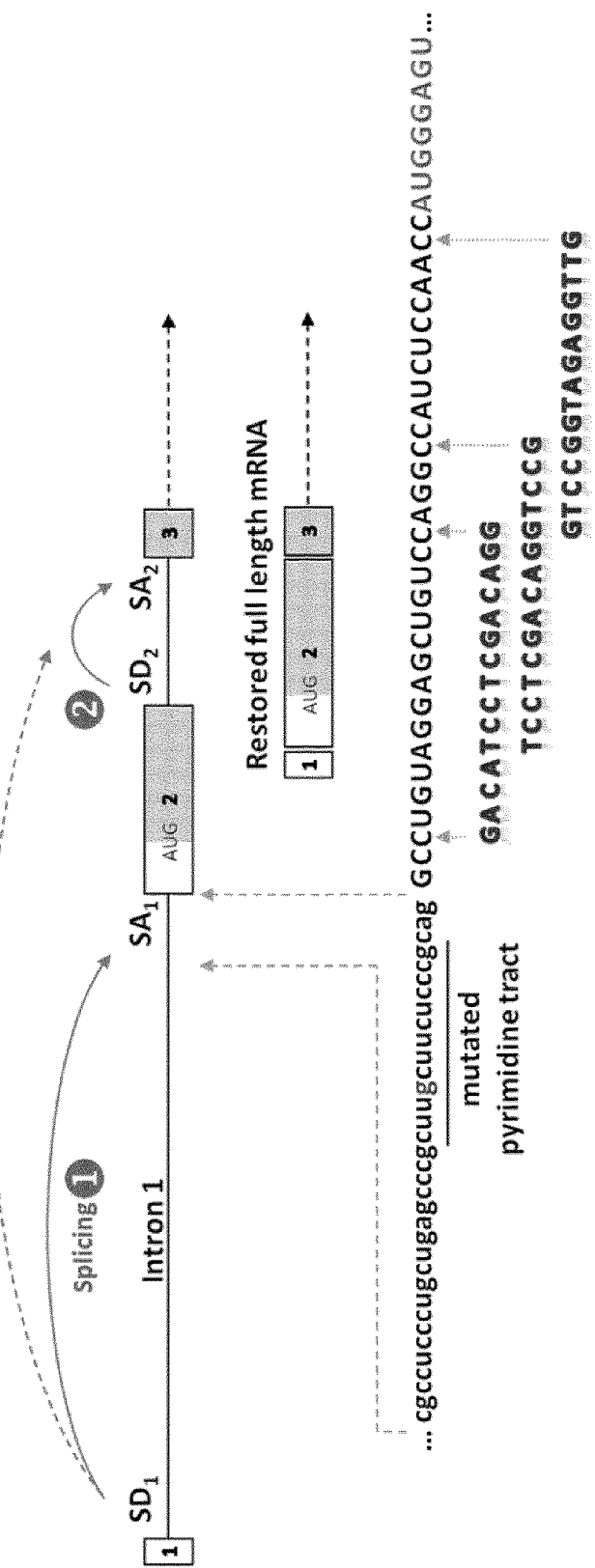
FIG. 4 represents the antisense target sequences for unwinding the acceptor splice site of exon 2 in c.-32 IVS1-13 T>G pre-mRNAs.

Accordingly with these assumptions, we proposed a method for rescuing full length GAA mRNA in patient cells with the c.-32 IVS1-13 T>G mutation by using antisense oligonucleotides (tricyclo-DNA) that were designed to anneal the 5' region of exon 2 (FIG. 4), which is involved in the putative hairpin described above, hence allowing to set free the acceptor splice site of exon 2 and its key upstream cis-elements (Py and Branch site).

Results

Figure 5:
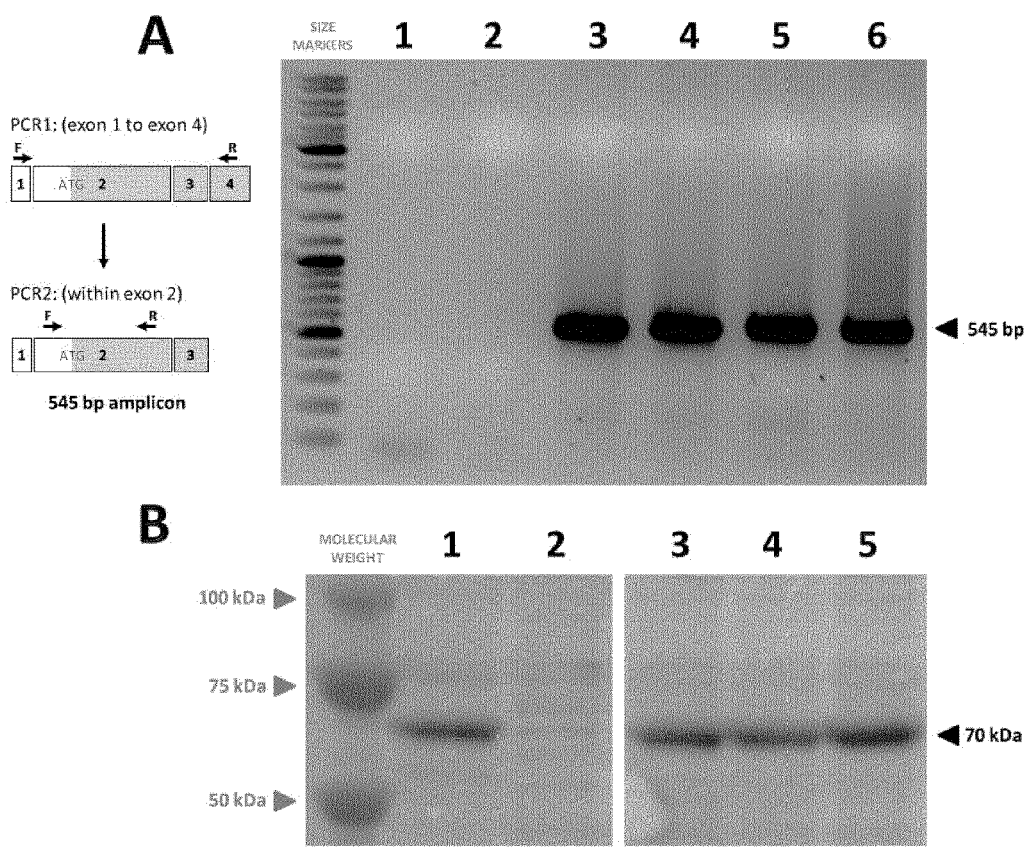
FIG. 5A is an agarose gel showing inclusion of exon 2 in GAA mRNAs from cells with the c.-32-13T>G mutation, after transfection with tricyclo-DNA antisense oligonucleotides in accordance with the present invention. The presence of exon 2 was assessed by nested RT-PCR (PCR1 from exon 1 to exon 4, followed by PCR2 within exon 2 giving rise to an amplicon of 545 base pairs). Lane 1 is a negative control where the RNA extract is replaced by H$_2$O. Lane 2 is untreated c.-32-13T>G cells. Lane 3 is healthy cells. Lanes 4, 5 and 6 are c.-32-13T>G cells transfected with AON1(tc-PS-DNA) having SEQ ID NO: 14 (and annealing to SEQ ID NO: 2), AON2(tc-PS-DNA) having SEQ ID NO.

Fibroblasts isolated from skin biopsies from GSD II patients with the c.-32 IVS1-13 mutation (the second mutation was c.546 T>G annealing the 3' donor splice site of exon 2) were grown in tissue culture and transfected with different amounts of tc-PS-DNA oligonucleotides (AON-1; AON-2; AON-3). Two days after transfection, cells were harvested and total RNA extracted in order to carry out RT-PCR analysis for assessing the integrity of the GAA mRNA. FIG. 5 shows subsequent amplicons obtained by using nested PCR with different sets of primers designed to assess the presence of exon 2 in the final mRNA. As expected, the set of primers (Fex1-Rex3 followed by F2-R3) allowed the detection of an amplicon of about 670 base-pairs encompassing exon 2. Such amplification did not occurred when using patient cells thus confirming that inclusion of exon 2 in the final mRNA was dramatically affected by the context of the mutation. However, in the presence of whatever tested AON (AON-1; AON-2; AON-3) targeting the [+3;+31] region, an amplicon of 670 by was detected straightforward indicative of GAA-mRNA rescue in patient cells (FIG. 5 A). Efficient translation of the rescued GAA mRNA was further confirmed by Western blot analysis using total protein extracts in treated cells (FIG. 5 B).

These experiments demonstrate that the c.-32 IVS1-13 T>G mutation can be rescue by means of splice-switching approaches using tricyclo-DNA oligomers in accordance with the present invention.

Example 2

Experiments similar to those described in Example 1 were carried out using 2'-O-Met oligomers (FIG. 6) thus confirming that different chemistries for the synthesis of synthetic antisense oligonucleotides can be used for GAA rescue in c.-32 IS1-13 GSD II cells.

Example 3

Figure 8:
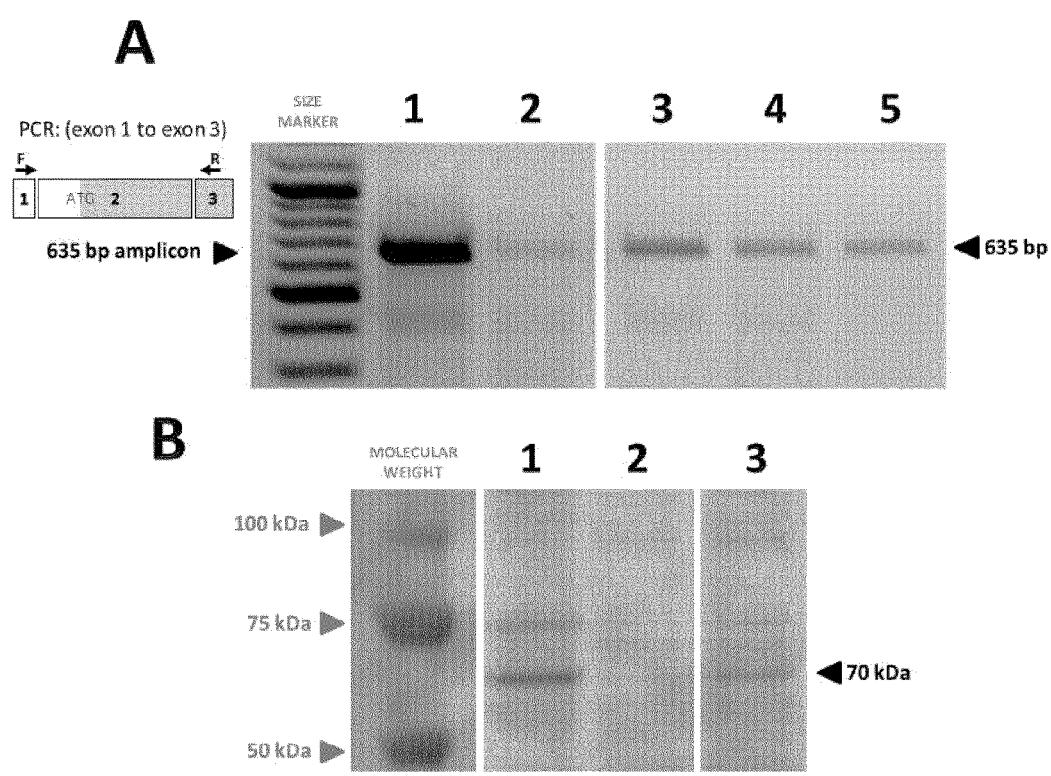

Experiments similar to those described in Examples 1 and 2 were carried out using the U7 system (FIG. 7) thus confirming that further antisense chemistries such as engineered snRNAs can be used for GAA rescue in c.-32 IS1-13 GSD II cells (FIG. 8).

Material & Methods

Cells:

Cultures of primary fibroblasts were derived from cutaneous biopsies of GSD II patients (Cell Bank of the Hospital Cochin). Reactives and culture media were products from GIBCO-Invitrogen unless otherwise indicated.

Skin fibroblasts were dissociated by incubation of cutaneous samples with collagenase type 1A (Sigma) and cultured in DMEM medium containing 10% foetal bovine serum (Sigma), 100 units/ml of penicillin, 100 µg/ml of streptomycin. When needed, these cells were converted into myogenic progenitors by transduction with a lentivector encoding for a doxycyclin-inducible MyoD gene. About 600 to 1200 viral particles per cell were incubated with fibroblasts for at least 4 hours. Transduced myo-fibroblasts and fibroblasts were used for transfection studies using antisense oligonucleotides.

Antisense Sequences Targeting the Exon 2 of the GAA Gene Product:

We designed 3 antisense sequences capable of annealing the 5' region of exon 2 of the human acid α-glucosidase pre-mRNA: first from nucleotide +3 to nucleotide +17, second from position +7 to +21 and third from position +17 to +31.

Antisense oligonucleotides were synthesised as 2'-O-Met oligomers and tricyclo (tc)-DNAs. Antisense sequences were also introduced into the U7OPT gene system by PCR as previously described (Goyenvalle and al., 2004). The resulting U7OPT-AS cassette was introduced in the pRR1 vector (for lentivector production) at the NheI and XbaI sites of restriction. The synthesis of tricyclo-nucleosides is known in the art, for example as described in Steffens R, et al., 1997, Helv Chim Acta 80:2426-2439; Renneberg D, et al., J Am Chem Soc, 2002, 124:5993-6002; WO 2013/053928; and references cited therein). The synthesis of 2'-O-methyl-phosphorothioate oligoribonucleotide (2'-O-Met) are also known for the skilled person in the art (WO 2013/112053 and references cited therein).

Transfection:

We used two concentrations (10 µg and 25 µg) of the three antisense oligonucleotides (AONs) to transfect fibroblasts from GSDII patients. Cells ($20 \times 10^3$ to $60 \times 10^3$) were plated into P6 wells. For each well, 10 or 25 µg of AON were diluted in 90 µl of DMEM, complexed with 12 µl of oligofectamin and incubated for 20 minutes. After addition of 800 µl of the free medium to the AON-mix, cells are incubated at 37° C. with this mix and diluted four hours later into another 1 ml of the proliferation medium.

Lentivector Production:

LV(U7opt-AS[+3;+31]) were produced as previously described (Dull T, et al.; J Virol, 1998, 72(11): 8463-8471; Benchaouir R., et al., Cell Stem Cell, 2007, 1(6):646-657).

Transduction:

Fibroblasts from GSDII patients ($25 \times 10^3$ cells) were incubated in 100 µl of DMEM supplied with different amounts (10; 5 or 1 µl) of a concentrated preparation of LV(U7opt-AS [+3;+31]) for 4 hours at 37° C. Then, cells were expanded in proliferation medium (DMEM supplemented with 10% of foetal bovine serum).

Nested PCR:

48 h after transfection, cells were collected and mRNA was extracted using RNeasy kit according to the manufacturer's instructions (Qiagen). 0.5 to 2 ng of total RNA sample was reverse transcribed into cDNA with the SuperScript II RT (SSIIR Invitrogen) primed by random hexamers according to the manufacturer. Exon 2 inclusion in the GAA mRNA was analyzed by nested RT-PCR. First PCR amplification was performed using 3 µg of cDNA in a 50 µl reaction with the external primers surrounding the exon 2 (Fex1-Rex3). The primary synthesis was performed with 30 cycles of 94° C. (30 seconds), 58° C. (1 minute), and 72° C. (2 minutes). Three micro liters of the first reaction were then reamplified in nested PCRs by 25 cycles of 94° C. (30 seconds), 58° C. (1 minute), and 72° C. (2 minutes) using the internal primers annealing inside the exon 2. The products of PCR were separated by electrophoresis in a 1.5% agarose gel stained with ethidium bromide.

```
Fex1:
                                          (SEQ ID NO: 7)
5' AGCTGACGGGGAAACTGAG 3'

Rex4:
                                          (SEQ ID NO: 8)
5' AAGGTCCCGGTTCCACAG 3'

Rex3:
                                          (SEQ ID NO: 9)
5' GCTCCTCGGAGAACTCCAC 3'

Fex2:
                                          (SEQ ID NO: 10)
5' CTGTCCAGGCCATCTCCA 3'

Rex2:
                                          (SEQ ID NO: 11)
5' AGTCTCCATCATCACGTCCA 3'
```

Western Blot Analysis:

The molecular mass of the human acid alpha-glucosidase was analyzed at day 3 post-transfection in the healthy, deficient and Tc-DNA treated fibroblasts. The cells were washed twice with PBS, trypsinized and pelleted. Protein lysates from cells were resolved by SDS-PAGE and transferred overnight to nitrocellulose. The specific protein was detected using a goat polyclonal antibody raised against human GAA. The immune complexes were visualized using a rabbit anti-goat immunoglobulin antiserum and chemiluminescence.

Histochemical Analysis:

Glycogen storage was determined by PAS staining. Control and treated cultured cells were rinsed in PBS for 5 min followed by incubation in Schiff reagent for 15 min at room temperature. They were analyzed by light microscopy.

The invention claimed is:

1. A nucleic acid molecule 10 to 50 nucleotides in length, complementary to a nucleotide sequence of the acid alpha-glucosidase pre-mRNA, said nucleic acid being able to correct the splicing of exon 2 of the acid alpha-glucosidase pre-mRNA, wherein the nucleic acid molecule comprises tricyclo-DNA-antisense oligonucleotides, tricyclo-phosphorothioate DNA-antisense oligonucleotides or U7- or U1-modified nucleic acid molecule, or a combination thereof, and further wherein said nucleic acid molecule comprises a nucleotide sequence at least 85% complementary to a sequence in the region defined by positions [+3;+45] of exon 2 of the GAA gene.

2. The nucleic acid molecule according to claim 1, wherein said nucleic acid molecule is able to correct the splicing of exon 2 of the human acid alpha-glucosidase pre-mRNA displaying the c.-32-13T>G mutation.

3. The nucleic acid molecule according to claim 1, wherein said nucleotide sequence is complementary to one or more of the sequences defined by positions 3-17, 7-21 or 17-31 in SEQ ID NO:1 or in a sequence having at least 90% homology with SEQ ID NO:1.

4. The nucleic acid molecule according to claim 1, wherein said nucleotide sequence is complementary to one of the sequences comprising SEQ ID NO:2, SEQ ID NO:3, SEQ ID NO:4, SEQ ID NO:5, SEQ ID NO:12 and SEQ ID NO:13.

5. The nucleic acid molecule according to claim 1, wherein said nucleic acid molecule comprises a nucleotide sequence complementary to a sequence comprised in the region defined by positions [+3;+31] of exon 2 of the human GAA gene (SEQ ID NO:1), wherein preferably said sequence comprised in the region defined by positions [+3;+31] of exon 2 of the human GAA gene (SEQ ID NO:1) has a length from at least 10 to at most 29 nucleotides.

6. The nucleic acid molecule according to claim 1, wherein said nucleic acid molecule comprises or is an antisense oligonucleotide.

7. The nucleic acid molecule according to claim 1, wherein the nucleic acid molecule comprises oligodeoxyribonucleotides.

8. The nucleic acid molecule according to claim 1, wherein said nucleic acid molecule comprises tricyclo-DNA-antisense oligonucleotides.

9. The nucleic acid molecule according to claim 1, wherein said nucleic acid molecule comprises tricyclo-phosphorothioate DNA-antisense oligonucleotides.

10. The nucleic acid molecule according to claim 1, wherein said nucleic acid molecule comprises a sequence selected from SEQ ID NO: 14, SEQ ID NO: 15, SEQ ID NO: 16, and SEQ ID NO: 17.

11. The nucleic acid molecule according to claim 1, wherein said nucleic acid molecule is linked to a modified U7 snRNA.

12. A method for the treatment of Pompe disease, comprising administering a nucleic acid molecule of claim 1 to a patient in need thereof.

13. The method according to claim 12, wherein the patient with Pompe disease harbors the c.-32 IVS1-13 T>G or an IVS1.-3 C>N mutation in the GAA gene.

14. A pharmaceutical composition comprising a nucleic acid molecule according to claim 1, in a pharmaceutically acceptable carrier.

15. The method accordingly to claim 12, wherein the patient with Pompe disease harbors the c.-32-13 T>G mutation in the human GAA gene.

16. The nucleic acid molecule according to claim 1, wherein all tc-nucleosides of said tricyclo-phosphorothioate DNA-antisense oligonucleotides are joined by inter nucleoside phosphorothioate linkages.

17. The nucleic acid molecule according to claim 10, wherein all tc-nucleosides of said tricyclo-phosphorothioate DNA-antisense oligonucleotides are joined by inter nucleoside phosphorothioate linkages.

18. The nucleic acid molecule according to claim 1, wherein said nucleic acid molecule comprises or consists of 2'-O-methyl-RNAs.

19. The nucleic acid molecule according to claim 1, wherein said nucleic acid is a 2'-O-methyl-RNA with full phosphorothioate backbone.

20. The nucleic acid molecule according to claim 1, wherein the nucleic acid molecule comprises oligoribonucleotides.

21. The nucleic acid molecule according to claim 1, wherein the nucleic acid molecule comprises morpholinos.

22. The nucleic acid molecule according to claim 1, wherein the nucleic acid molecule comprises LNA oligonucleotides.

* * * * *

SEQUENCE LISTING

```
<160> NUMBER OF SEQ ID NOS: 18

<210> SEQ ID NO 1
<211> LENGTH: 578
<212> TYPE: DNA
<213> ORGANISM: homo sapiens

<400> SEQUENCE: 1
gcctgtagga gctgtccagg ccatctccaa ccatgggagt gaggcacccg ccctgctccc      60
accggctcct ggccgtctgc gccctcgtgt ccttggcaac cgctgcactc ctggggcaca     120
tcctactcca tgatttcctg ctggttcccc gagagctgag tggctcctcc ccagtcctgg     180
aggagactca cccagctcac cagcagggag ccagcagacc agggccccgg gatgcccagg     240 cacacccccgg ccgtcccaga gcagtgccca cacagtgcga cgtcccccccc aacagccgct     300 tcgattgcgc ccctgacaag gccatcaccc aggaacagtg cgaggcccgc ggctgttgct     360
acatccctgc aaagcagggg ctgcagggag cccagatggg gcagccctgg tgcttcttcc     420
cacccagcta ccccagctac aagctggaga acctgagctc ctctgaaatg ggctacacgg     480
ccaccctgac ccgtaccacc cccaccttct tccccaagga catcctgacc ctgcggctgg     540
acgtgatgat ggagactgag aaccgcctcc acttcacg                              578

<210> SEQ ID NO 2
<211> LENGTH: 15
<212> TYPE: RNA
<213> ORGANISM: artificial
<220> FEATURE:
<223> OTHER INFORMATION: target sequence

<400> SEQUENCE: 2
```
cuguaggagc ugucc                                                    15

<210> SEQ ID NO 3
<211> LENGTH: 15
<212> TYPE: RNA
<213> ORGANISM: artificial
<220> FEATURE:
<223> OTHER INFORMATION: target sequence

<400> SEQUENCE: 3
aggagcuguc caggc                                                    15

<210> SEQ ID NO 4
<211> LENGTH: 15
<212> TYPE: RNA
<213> ORGANISM: artificial
<220> FEATURE:
<223> OTHER INFORMATION: target sequence

<400> SEQUENCE: 4
caggccaucu ccaac                                                    15

<210> SEQ ID NO 5
<211> LENGTH: 44
<212> TYPE: RNA
<213> ORGANISM: artificial
<220> FEATURE:
<223> OTHER INFORMATION: target sequence

<400> SEQUENCE: 5
cuguaggagc uguccaggcc aucuccaacc augggaguga ggca                    44

<210> SEQ ID NO 6
<211> LENGTH: 57
<212> TYPE: RNA
<213> ORGANISM: artificial
<220> FEATURE:
<223> OTHER INFORMATION: U7-modified antisense oligonucleotide

<400> SEQUENCE: 6
guuggagaug gccuggacag cuccuacagg uuuucugacu ucggucggaa aaccccu      57

<210> SEQ ID NO 7
<211> LENGTH: 19
<212> TYPE: DNA
<213> ORGANISM: artificial
<220> FEATURE:
<223> OTHER INFORMATION: primer

<400> SEQUENCE: 7
agctgacggg gaaactgag                                                19

<210> SEQ ID NO 8
<211> LENGTH: 18
<212> TYPE: DNA
<213> ORGANISM: artificial
<220> FEATURE:
<223> OTHER INFORMATION: primer

<400> SEQUENCE: 8
aaggtcccgg ttccacag                                                 18

<210> SEQ ID NO 9
<211> LENGTH: 19
<212> TYPE: DNA
<213> ORGANISM: artificial

```
<220> FEATURE:
<223> OTHER INFORMATION: primer

<400> SEQUENCE: 9
gctcctcgga gaactccac                                                19

<210> SEQ ID NO 10
<211> LENGTH: 18
<212> TYPE: DNA
<213> ORGANISM: artificial
<220> FEATURE:
<223> OTHER INFORMATION: primer

<400> SEQUENCE: 10
ctgtccaggc catctcca                                                 18

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
agtctccatc atcacgtcca                                               20

<210> SEQ ID NO 12
<211> LENGTH: 29
<212> TYPE: RNA
<213> ORGANISM: artificial
<220> FEATURE:
<223> OTHER INFORMATION: target sequence

<400> SEQUENCE: 12
cuguaggagc uguccaggcc aucuccaac                                     29

<210> SEQ ID NO 13
<211> LENGTH: 43
<212> TYPE: RNA
<213> ORGANISM: artificial
<220> FEATURE:
<223> OTHER INFORMATION: target sequence

<400> SEQUENCE: 13
cuguaggagc uguccaggcc aucuccaacc augggaguga ggc                     43

<210> SEQ ID NO 14
<211> LENGTH: 15
<212> TYPE: DNA
<213> ORGANISM: artificial
<220> FEATURE:
<223> OTHER INFORMATION: antisense oligonucleotide AON1

<400> SEQUENCE: 14
ggacagctcc tacag                                                    15

<210> SEQ ID NO 15
<211> LENGTH: 15
<212> TYPE: DNA
<213> ORGANISM: artificial
<220> FEATURE:
<223> OTHER INFORMATION: antisense oligonucleotide AON2

<400> SEQUENCE: 15
gcctggacag ctcct                                                    15
```

```
<210> SEQ ID NO 16
<211> LENGTH: 15
<212> TYPE: DNA
<213> ORGANISM: artificial
<220> FEATURE:
<223> OTHER INFORMATION: antisense oligonucleotide AON3

<400> SEQUENCE: 16
gttggagatg gcctg                                                    15

<210> SEQ ID NO 17
<211> LENGTH: 29
<212> TYPE: DNA
<213> ORGANISM: artificial
<220> FEATURE:
<223> OTHER INFORMATION: antisense oligonucleotide

<400> SEQUENCE: 17
gttggagatg gcctggacag ctcctacag                                     29

<210> SEQ ID NO 18
<211> LENGTH: 71
<212> TYPE: RNA
<213> ORGANISM: artificial
<220> FEATURE:
<223> OTHER INFORMATION: U7opt-AS[+3;+31]

<400> SEQUENCE: 18
guuggagaug gccuggacag cuccuacaga auuuuuggag cagguuuucu gacuucgguc    60
ggaaaacccc u                                                        71
```